(12) United States Patent
Ishizuka et al.

(10) Patent No.: US 10,122,953 B2
(45) Date of Patent: Nov. 6, 2018

(54) IMAGING MODULE

(71) Applicant: FUJIKURA LTD., Tokyo (JP)

(72) Inventors: Takeshi Ishizuka, Sakura (JP); Hideaki Usuda, Sakura (JP)

(73) Assignee: FUJIKURA LTD., Koto-ku, Tokyo (JP)

( * ) Notice: Subject to any disclaimer, the term of this patent is extended or adjusted under 35 U.S.C. 154(b) by 39 days.

(21) Appl. No.: 15/363,759

(22) Filed: Nov. 29, 2016

(65) Prior Publication Data

US 2017/0155860 A1 Jun. 1, 2017

(30) Foreign Application Priority Data

Nov. 30, 2015 (JP) .................. 2015-234028
Nov. 28, 2016 (JP) .................. 2016-230523

(51) Int. Cl.
| | | |
|---|---|---|
| H04N 5/374 | (2011.01) | |
| H04N 5/225 | (2006.01) | |
| A61B 1/05 | (2006.01) | |
| H01R 13/22 | (2006.01) | |
| H01R 13/631 | (2006.01) | |

(Continued)

(52) U.S. Cl.
CPC ............. *H04N 5/374* (2013.01); *A61B 1/051* (2013.01); *H01R 13/22* (2013.01); *H01R 13/405* (2013.01);

(Continued)

(58) Field of Classification Search
CPC .... H01R 13/631; H01R 13/405; H01R 13/22; H01R 2201/12
See application file for complete search history.

(56) References Cited

U.S. PATENT DOCUMENTS 6,567,115 B1   5/2003 Miyashita et al.
2011/0249106 A1  10/2011 Makino et al.
(Continued)

FOREIGN PATENT DOCUMENTS

| EP | 2 790 218 A1 | 10/2014 |
|---|---|---|
| JP | 62-98318 A | 5/1987 |
| JP | 2000-075218 A | 3/2000 |
| JP | 2000-92477 A | 3/2000 |

(Continued)

OTHER PUBLICATIONS

Foreign Japanese Office Action for JP 2015-234028 dated Oct. 11, 2016.

(Continued)

*Primary Examiner* — Christopher K Peterson
(74) *Attorney, Agent, or Firm* — Sughrue Mion, PLLC

(57) ABSTRACT

An imaging module of the invention includes: a solid-state image sensing device including an imaging-device terminal; a connector having a first end face, a second end face located opposite to the first end face, and a side face orthogonal to the first end face, the connector including: a main body serving as an insulating member, an implanted conductor that is implanted in an inside of the main body, a first mounting terminal that is electrically connected to the imaging-device terminal and the implanted conductor and is provided on the first end face, a second mounting terminal that is provided on the side face and constitutes part of the implanted conductor, and a third mounting terminal that is provided on the second end face and constitutes part of the implanted conductor; and a signal cable electrically connected to the second mounting terminal.

11 Claims, 15 Drawing Sheets

(51) Int. Cl.
*H01R 13/405* (2006.01)
*H01R 12/53* (2011.01)
*H01R 4/02* (2006.01)

(52) U.S. Cl.
CPC ......... *H01R 13/631* (2013.01); *H04N 5/2257* (2013.01); *H01R 4/028* (2013.01); *H01R 12/53* (2013.01); *H01R 2201/12* (2013.01)

(56) References Cited

U.S. PATENT DOCUMENTS

2014/0124256 A1* 5/2014 Hattori .................. H01G 2/065
174/260
2016/0029879 A1* 2/2016 Ishikawa ............ A61B 1/00114
600/110

FOREIGN PATENT DOCUMENTS

| JP | 2000-199863 A | 7/2000 |
| JP | 2011-188375 A | 9/2011 |
| JP | 2011-217887 A | 11/2011 |
| JP | 2013-118337 A | 6/2013 |
| WO | 2015/019671 A1 | 2/2015 |

OTHER PUBLICATIONS

Communication dated Oct. 17, 2017 from the Japanese Patent Office in counterpart application No. 2016-230523.
Communication dated Dec. 19, 2017 from the Japanese Patent Office in counterpart Japanese application No. 2016-230523.

* cited by examiner

IMAGING MODULE

CROSS REFERENCE TO RELATED APPLICATIONS

This application claims priority from Japanese Patent Application No. 2015-234028 filed on Nov. 30, 2015, and Japanese Patent Application No. 2016-230523 filed on Nov. 28, 2016, the contents of which are incorporated herein by reference in their entirety.

BACKGROUND OF THE INVENTION

Field of the Invention

The present invention relates to an imaging module.

Description of the Related Art

Conventionally, a small imaging module utilizing a solid-state image sensing device is known.

Such imaging module is used in, for example, an endoscope.

As the configuration of the imaging module, a configuration is known which uses a flexible substrate that is provided with a solid-state image sensing device in which a through-hole interconnection is formed (for example, refer to Japanese Unexamined Patent Application, First Publication No. 2011-217887, and hereinbelow referred to as Patent Document 1).

In the imaging module disclosed in Patent Document 1, the flexible substrate is bent toward the opposite side of the imaging surface (toward the rear side of the solid-state image sensing device) from both sides of the portion of the flexible substrate on which the solid-state image sensing device is mounted so that the shape (projected shape) of the flexible substrate does not exceed the region defined by the outer shape of the solid-state image sensing device as seen from the imaging surface of the solid-state image sensing device.

Furthermore, as another configuration of an imaging module, a configuration in which a film is formed on a T-shaped multilayer ceramic substrate is known in which a solid-state image sensing device, an electronic component, a terminal connected to a signal cable, and wirings connected to a solid-state image sensing device are formed on the film (for example, refer to Japanese Unexamined Patent Application, First Publication No. 2000-199863, and hereinbelow referred to as Patent Document 2).

In the step of manufacturing the imaging module using the flexible substrate disclosed in Patent Document 1, for example, there are problems in that the wirings formed on the flexible substrate are likely to be broken and it is difficult to stabilize the shape or the size of the wirings, and the reliability is low.

In the imaging module using the multilayer ceramic substrate which is disclosed in Patent Document 2, for example, the reliability thereof is high; however, it is necessary to provide a quite large number of layers in order to obtain the T-shaped multilayer structure.

Consequently, the multilayer ceramic substrate is not suitable to reduce the size of the imaging module, and there is a problem in that the cost of manufacturing the imaging module remarkably increases.

In other cases, the T-shaped multilayer structure can be manufactured by adhesively attaching a plurality of layers to each other; however, in this case, although the number of layers decreases, it is extremely difficult to maintain the accuracy of the positions at which the layers are adhesively attached to each other.

In the case of employing the above-described step of adhesively attaching the layers, adjacent layers are adhesively attached with an adhesive interposed therebetween. However, the adhesive exudes from between the layers which are attached to each other, and also it is difficult to stabilize the amount of adhesive exuding from between the layers.

As a result, it is not easy to manufacture the T-shaped multilayer structure above-described step of adhesively attaching the layers.

SUMMARY OF THE INVENTION

One aspect of the invention was conceived in view of the above-described conventional circumstances and has an object thereof to provide an ultrafine imaging module which can be easily manufactured while maintaining a high degree of reliability.

In order to realize the aforementioned object, an imaging module according to one aspect of the invention: includes: a solid-state image sensing device including an imaging-device terminal; a connector having a first end face, a second end face located opposite to the first end face, and a side face orthogonal to the first end face, the connector including: a main body serving as an insulating member, an implanted conductor that is implanted in an inside of the main body, a first mounting terminal that is electrically connected to the imaging-device terminal and the implanted conductor and is provided on the first end face, a second mounting terminal that is provided on the side face and constitutes part of the implanted conductor, and a third mounting terminal that is provided on the second end face and constitutes part of the implanted conductor; and a signal cable electrically connected to the second mounting terminal.

In the imaging module according to one aspect of the invention, the shape of the connector may be a rectangular parallelepiped having at least the first end face, the second end face, and the side face.

In the imaging module according to one aspect of the invention, the connector may include: a first side face and a second side face which are orthogonal to the first end face, and a groove provided between the first side face and the second side face, the second mounting terminal may be provided in the groove, and the signal cable may be located in the groove and may be electrically connected to the second mounting terminal.

In the imaging module according to one aspect of the invention, the second side face may be orthogonal to the first end face and the first side face, a first virtual extension surface of the first side face and a second virtual extension surface of the second side face intersect with each other at an intersection point, the groove may be a region surrounded by walls connected to the first side face and the second side face, the first virtual extension surface, and the second virtual extension surface, and the second mounting terminal may be electrically connected to the signal cable inside the groove.

The imaging module according to one aspect of the invention may further include: a plurality of grooves, each of which is provided at a corner region of the connector; and a plurality of second mounting terminals, each of which is provided so as to correspond to one groove, wherein each second mounting terminal may be provided inside one groove, and the plurality of the second mounting terminals may be located at the positions that face each other.

In the imaging module according to ne aspect of the invention, the connector and the signal cable may be positioned within a region surrounded by an external outline of the solid-state image sensing device as seen in the direction from the solid-state image sensing device to the second end face.

In the imaging module according to one aspect of the invention, the first mounting terminal may constitute part of the implanted conductor.

In the imaging module according to one aspect of the invention, the implanted conductor may extend from the first end face to the second end face and may be implanted in the inside of the main body.

In the imaging module according to one aspect of the invention, the implanted conductor may include: an internal conductor that extends in a direction from the first end face to the second end face in the inside of the main body; and a connection conductor that connects the internal conductor and the second mounting terminal in the inside of the main body.

The imaging module according to an aspect of the invention may further include: a fourth mounting terminal provided on the second end face; and an electronic component provided on the fourth mounting terminal and connected thereto.

The imaging module according to one aspect of the invention may further include: solder that electrically connects the third mounting terminal and the signal cable, wherein the third mounting terminal may include a terminal-front-end portion, and the terminal-front-end portion may be located at a position apart from a connection surface between the second mounting terminal and the signal cable, the signal cable may include: a conductor, a coated portion, and a cable boundary portion located at a boundary between the conductor and the coated portion, the cable boundary portion may be located outside the second end face, and the solder may coat the third mounting terminal and the conductor so as to form a curved surface that extends from the terminal-front-end portion to the cable boundary portion.

Effects of the Invention

As described above, according to the aspect of the invention, it is possible to provide an ultrafine imaging module which can be easily manufactured while maintaining a high degree of reliability.

DETAILED DESCRIPTION OF THE INVENTION

Figure 1:
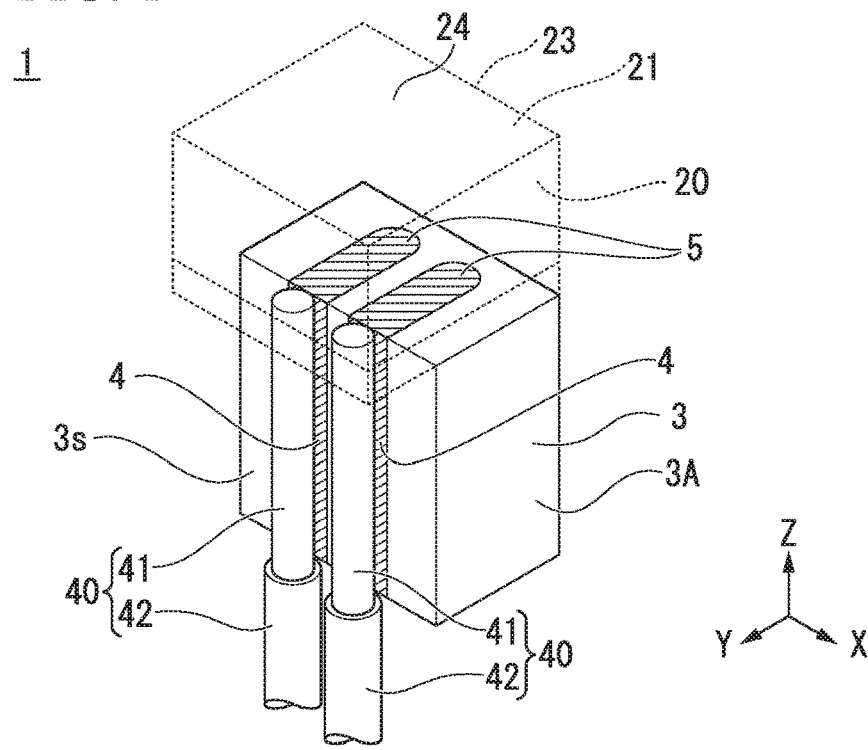
FIG. 1 is a perspective view showing a configuration of an imaging module according to a first embodiment of the invention.

Hereinafter, an embodiment of the invention will be described with reference to drawings.

In the drawings showing the embodiment of the invention, in order for the respective components to be of understandable size in the drawings, the dimensions and the proportions of the components are modified as needed compared with the real components.

(First Embodiment)

FIG. 1 is a perspective view showing a configuration of an imaging module 1 according to a first embodiment of the invention.

Figure 2:
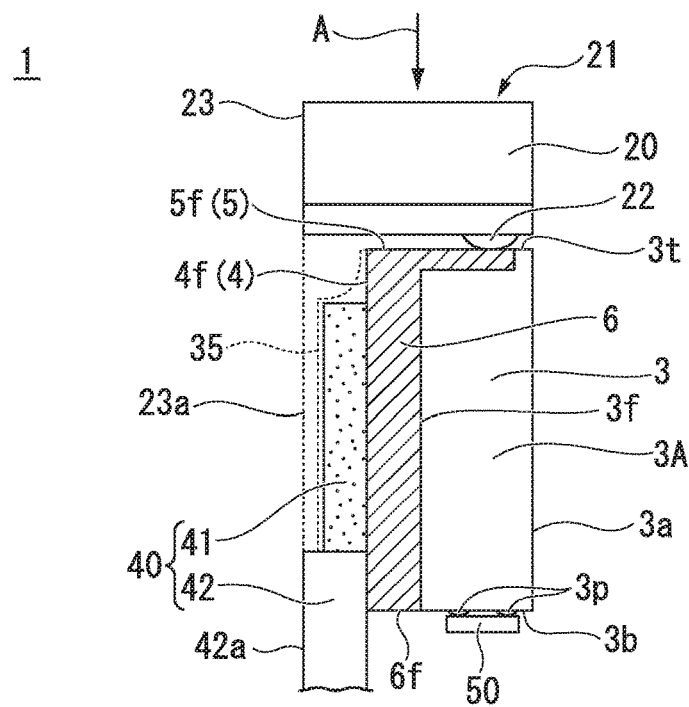
FIG. 2 is a cross-sectional view showing the configuration of the imaging module according to the first embodiment of the invention.

FIG. 2 is a cross-sectional view showing the configuration of the imaging module 1 according to the first embodiment of the invention.

The imaging module 1 includes: a solid-state image sensing device 20; a connector 3, and two signal cables 40 (first signal cable and second signal cable).

In the imaging module 1, the solid-state image sensing device 20 is electrically connected to the two signal cables 40 through the connector 3.

As shown in FIG. 2, the imaging module 1 includes a capacitor 50 (electronic component).

The solid-state image sensing device 20 includes: a light-receiving face 21 which is located at the upper surface of the solid-state image sensing device 20; and imaging-device terminals 22 which are provided on the lower surface of the solid-state image sensing device 20.

A lens unit such as an object lens may be mounted on the light-receiving face 21.

The imaging-device terminals 22 serve as terminals that are to be connected to mounting pads which are provided on the upper surface 3t of the connector 3 and will be described below.

As the solid-state image sensing device 20, for example, a CMOS (complementary metal oxide semiconductor) is preferably used.

Figure 3:
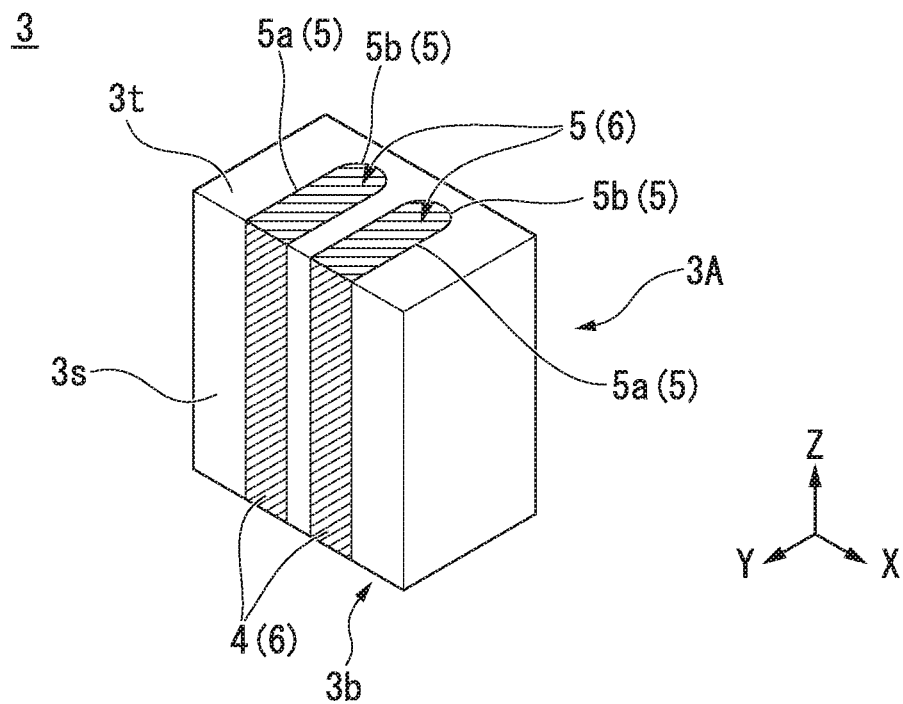
FIG. 3 is a perspective view showing a connector that constitutes the imaging module according to the first embodiment of the invention.

FIG. 3 is a perspective view showing the connector 3.

In FIG. 3, the length of one side of the connector (in the X-direction and the Y-direction) is less than or equal to 1 mm.

The connector 3 includes: a main body 3A that functions as an insulator (insulating member); two implanted terminals 4 (second mounting terminal, first implanted terminal, second implanted terminal); two mounting pads 5 (first mounting terminal, first mounting pad, second mounting pad); two implanted conductors 6 (first implanted conductor, second implanted conductor); and mounting pads 3p (fourth mounting terminal).

The main body 3A has: an upper surface 3t (first end face); a lower surface 3b (second end face) that is located on the opposite side of the upper surface 3t; and a side face 3s that is orthogonal to the upper surface 3t.

The mounting pads 5 are formed on the upper surface 3t and are electrically connected to the imaging-device finals 22 and the implanted conductors 6.

In the inside of the connector 3, the implanted conductors 6 are provided so as to extend in the Z-direction, that is, in the direction from the upper surface 3t to the lower surface 3b.

Each implanted conductor 6 integrally forms the implanted terminal 4 and the mounting pad 5.

In other words, the implanted terminal 4 constitutes part of the implanted conductor 6, and the mounting pad 5 constitutes part of the implanted conductor 6. More specifically, the implanted conductor 6 is an integrally molded member formed in the connector 3.

In FIG. 2, the integrally molded member is conductor surrounded by: the top surface 5f of mounting pad 5; the surface 4f of the implanted terminal 4 which is continuously connected to the top surface 5f of mounting pad 5; the end face 6f of the implanted conductor 6 which is continuously connected to the surface 4f of the implanted terminal 4 and is exposed at the lower face 3b; and a contact surface 3f which is continuously connected to the end face 6f and the top surface 5f and is located between the implanted conductor 6 and the insulating member (main body 3A).

Particularly, the portion at which the implanted conductor 6 is exposed on the side face 3s is the implanted terminal 4.

The portion at which the implanted conductor 6 is exposed on the upper surface 3t is the mounting pad 5.

Similar to the implanted conductor 6, the implanted terminals 4 extend in the Z-direction, that is, in the direction from the upper surface 3t to the lower surface 3b.

The implanted terminals 4 are exposed at the side face 3s and to the outside of the connector 3.

The signal cables 40 which will be described later are electrically connected to the implanted terminals 4.

In the example shown in FIG. 2, the implanted conductor 6 includes the mounting pads 5 that linearly extend in the Y-direction; and the implanted terminals 4 that linearly extend in the Z-direction. The implanted conductor is formed in an inverted L-shape.

The shape of the connector 3 is a rectangular parallelepiped having at least the upper surface 3t, the lower surface 3b, and the side face 3s.

Specifically, the rectangular parallelepiped has six surfaces of the upper surface 3t, the lower surface 3b, and four side surfaces that are located between the upper surface 3t and the lower surface 3b.

The side face 3s is one of the four side surfaces.

As shown in FIG. 2, when seen in a plan view (a plan view as seen the Z-direction), the mounting pad 5 provided on the upper surface 3t of the connector 3 has a wiring pattern corresponding to the design of the solid-state image sensing device 20 (placement of the imaging-device terminal 22) such that the imaging-device terminal 22 overlaps the mounting pad 5.

Because of this, when the solid-state image sensing device 20 is mounted on the upper surface 3t, the imaging-device terminals 22 and the mounting pads 5 are electrically connected to each other.

In the configurations shown in FIGS. 1 to 3, the mounting pads 5 are implanted in the main body 3A; however, the invention is not limited to this configuration.

For example, the mounting pads 5 may be formed on the upper surface 3t of the main body 3A by use of a method such as a printing method.

That is, the mounting pad 5 may be a thin-film pad formed on the upper surface 3t.

Particularly, as compared with the case where part of the implanted conductor that extends in the Z-direction is a mounting pad (the implanted conductor exposed at the upper surface 3t), in the case of forming the mounting pads by patterning using, for example, a printing method, since the mounting pads are formed on the upper surface 3t, the diameter or the width of the mounting pad can easily coincide with the diameter of the imaging-device terminal 22.

In the example shown in FIG. 3, each of the mounting pads 5 includes an extending pad 5a and a front-end pad 5b located at the end of the extending pad.

Specifically, the extending pad 5a. extends in the Y-direction from the implanted terminal 4 to the front-end pad 5b, and the width of the extending pad 5a in the X-direction is a constant width.

The front-end pad 5b forms part of the extending pad 5a and is formed in a semicircular shape.

Similar to the upper wiring 33 according to the second embodiment which will be described later, the width of the extending pad 5a may be different from the width of the implanted terminal 4.

In the case of forming the mounting pads 5 by patterning using, for example, a printing method, the extending pad 5a may be a thin-film wiring (relocation wiring, a thin film having a wiring pattern) which is patterned on the upper surface 3t.

In this case, a relocation wiring that connects the implanted terminal 4 and the forming portion of the front-end pad 5b corresponding to the position of the imaging-device terminal 22 is formed on the upper surface 3t.

As shown in FIGS. 1 and 2, as seen in the direction (arrow A) from the solid-state image sensing device 20 to the lower surface 3b, the connector 3 and the signal cables 40 are located within the region 24 surrounded by the external outline 23 of the solid-state image sensing device 20.

In the plan view showing the solid-state image sensing device 20 as seen in the direction of the arrow A, part of the connector 3 and part of the signal cable 40 do not protrude from the solid-state image sensing device 20 to the outside.

Regarding the cross-sectional surface orthogonal to the arrow A, the cross-sectional surface of the solid-state image sensing device 20 overlaps the cross-sectional surfaces of the connector 3 and the signal cable 40.

In the embodiment, as shown in FIG. 2, the extended line 23a of the external outline 23 of the solid-state image sensing device 20 that extends in the Z-direction coincides with the outer end 42a (left end in FIG. 2) of the coated portion 42 of the signal cable 40; however, the invention is not limited to this configuration.

It is only necessary that the signal cables 40 are arranged within le region 24 surrounded by the external outline 23.

Furthermore, in the embodiment, as shown in FIG. 2, the position of the right end 3a of the connector 3 in the Y-direction coincides with the external outline 23; however, the invention is not limited to this configuration.

It is only necessary that the connector 3 is arranged within the region 24 surrounded by the external outline 23.

As a material used to form the main body 3A, a publicly known material is used.

For example, a sintered member such as alumina or LTCC may be used.

As a material used to form the main body 3A, for example, a glass epoxy substrate (FR-4), a ferrule substrate, a silicon substrate, or a glass substrate may be adopted.

As a material used to form the implanted terminal 4, a publicly known material is used.

For example, copper, silver, nickel, gold, tungsten, or the like may be adopted as a material used to form the implanted terminal 4.

As shown in FIGS. 1 and 2, each of the two signal cables 40 includes a conductor 41 and a coated portion 42 (insulator).

As the signal cable 40, a generally-known signal cable having a single core is used.

The conductor 41 extends parallel to the implanted terminal 4 and is connected to the implanted terminal 4.

Solder 35 is provided so as to coat the conductor 41 and the implanted terminal 4.

That is, the conductor 41 and the implanted terminal 4 are soldered and electrically connected to each other.

The conductor 41, the implanted terminal 4, and the solder 35 constitute an electrically connected portion.

As shown in FIG. 2, the mounting pads 3p (fourth mounting terminal) are provided on the lower surface 3b of the connector 3.

The terminal (electrode) of the capacitor 50 is connected to the mounting pad 3p via solder in a state where the capacitor 50 is mounted on the lower surface 3b of the connector 3, and the capacitor 50 is electrically connected to the connector 3.

In other cases, a wiring or the like (including an electrode or a terminal) which is electrically connected to the implanted terminal 4 may be formed on the lower surface 3b, in this case, the wiring can be connected to the mounting pad 3p.

Consequently, it is possible to electrically connect the solid-state image sensing device 20, the capacitor 50, and the signal cables 40 through the mounting pads 5, the implanted terminals 4, and the mounting pads 3p which are provided on the connector 3.

In other cases, the electronic component which is mounted on the mounting pads 3p is not limited to the capacitor 50, an electrical resistance or a coil may be mounted on the mounting pads 3p.

Next, an example of a method of forming of the connector 3 will be described with reference to FIG. 4.

Figure 4:
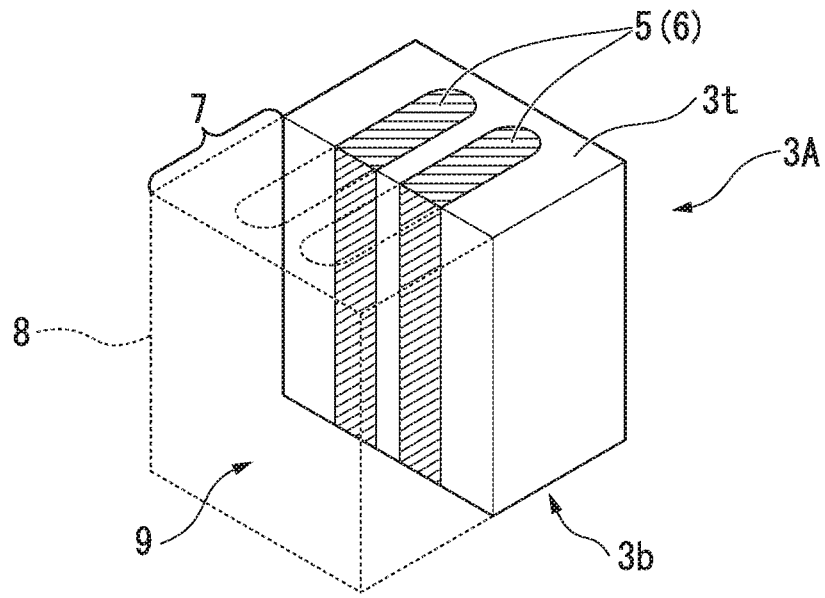
FIG. 4 is view showing a state before the connector that constitutes the imaging module according to the first embodiment of the invention is formed, and is a perspective view showing a shaped member before a removal region is removed.

FIG. 4 shows the outer shape of the shaped member (the member serves as the connector 3 by a subsequent process) before a removal region 7 is removed. Here, the removal region 7 means the portion which is to be removed by the step described below, in other words, the removal portion can be referred to as a to-be-removed portion.

As shown in FIG. 4, before the removal region 7 is removed, a through hole is provided in an insulation material that constitutes the main body 3A, the through hole is filled with an electroconductive material, and a conductive structure that functions as the implanted conductor 6 is implanted in the through hole.

Thereafter, the connector 3 is formed by grinding the removal region 7, that is, by removing (working) the portion 9 indicated by the dotted line 8, and the implanted terminals 4 are exposed at the side face 3s.

In other words, the implanted terminal 4 can be referred to as an exposed terminal at which the aforementioned implanted conductor 6 is partially exposed.

The side face 3s can be referred to as a removed surface.

Such removed surface is a grinding surface formed by grinding and can be said to be a surface having a grinding trace that occurs due to contact between a grinding tool and the main body 3A.

The implanted terminal 4 has a structure which is completely different from that of the coated film formed on a substrate surface by use of a publicly known film formation method.

Particularly, the implanted terminal 4 is part of the implanted conductor 6 that is implanted in the inside of the main body 3A.

For example, in the case of applying a sintered member serving as a member constituting the connector 3 to the aforementioned method, it is believed that the connector 3 is formed by use of the following material and method.

Firstly, by use of an insulation material such as ceramic, a main body 3A (insulating member) having a through hole is formed.

Next, the through hole of the main body 3A is filled with an electroconductive material, and a filled via is formed.

Thereafter, in a sintering process, the insulating member and the filled via are sintered, and a sintered member is thereby formed.

Subsequently, the removal region 7 is removed by use of a known grinding tool.

As a result, it is possible to form the connector 3 having the implanted terminals 4 that are exposed at the side face 3s.

For example, in the ease of applying a glass epoxy substrate or a ferrule substrate, which serves as a member constituting the connector 3, to the aforementioned method, it is believed that the connector 3 is formed by use of the following material and method.

Firstly, a through hole is formed on a glass epoxy substrate or a ferrule substrate which serves as the main body 3A (insulating member).

Next, a filled via is formed in the through hole of the main body 3A by a method, such as, for example, plating or the like.

Subsequently, the removal region 7 is removed by use of a known grinding tool.

As a result, it is possible to form the connector 3 having the implanted terminals 4 that are exposed at the side face 3s.

For example, in the case of applying a silicon substrate or a glass substrate, which serves as a member constituting the connector 3, it is believed that the connector 3 is formed by use of the following material and method.

Firstly, a through hole is formed on a substrate which serves as the main body 3A (insulating member).

Next, a through-hole interconnection (through silicon via, TSV) is formed in the through hole of the main body 3A.

Subsequently, the removal region 7 is removed by use of a known grinding tool.

As a result, it is possible to form the connector 3 having the implanted terminals 4 that are exposed at the side face 3s.

According to the imaging module 1 of the above-described embodiment, since the connector 3 is used which s different from a flexible substrate in which wiring is likely to be broken, connection stability between the signal cables 40 and the solid-state image sensing device 20 is ensured, and it is possible to maintain a high degree of reliability.

Moreover, as described above, since the structure is adopted in which the signal cables 40 are connected to the implanted terminals 4 exposed at the side face of the connector 3, it is possible to reduce the number of layers constitute the connector 3.

Furthermore, it is possible to easily manufacture the connector 3.

Particularly, in the case of a ultrafine module such that an outer diameter of an imaging module is, for example, 2 mm, as a result of applying the imaging module 1 according to the embodiment to the imaging module, the imaging module 1 can be arranged in a limited space, and it significantly contributes to miniaturization of the module.

Additionally, since the shape of the connector 3 is a rectangular parallelepiped, it is possible to realize a simple structure, and it is possible to easily manufacture the connector 3.

Also, since the connector 3 and the signal cables 40 are located within the region 24 surrounded by the external outline 23 of the solid-state image sensing device 20, it significantly contributes to miniaturization of the module.

(Second Embodiment)

Figure 5:
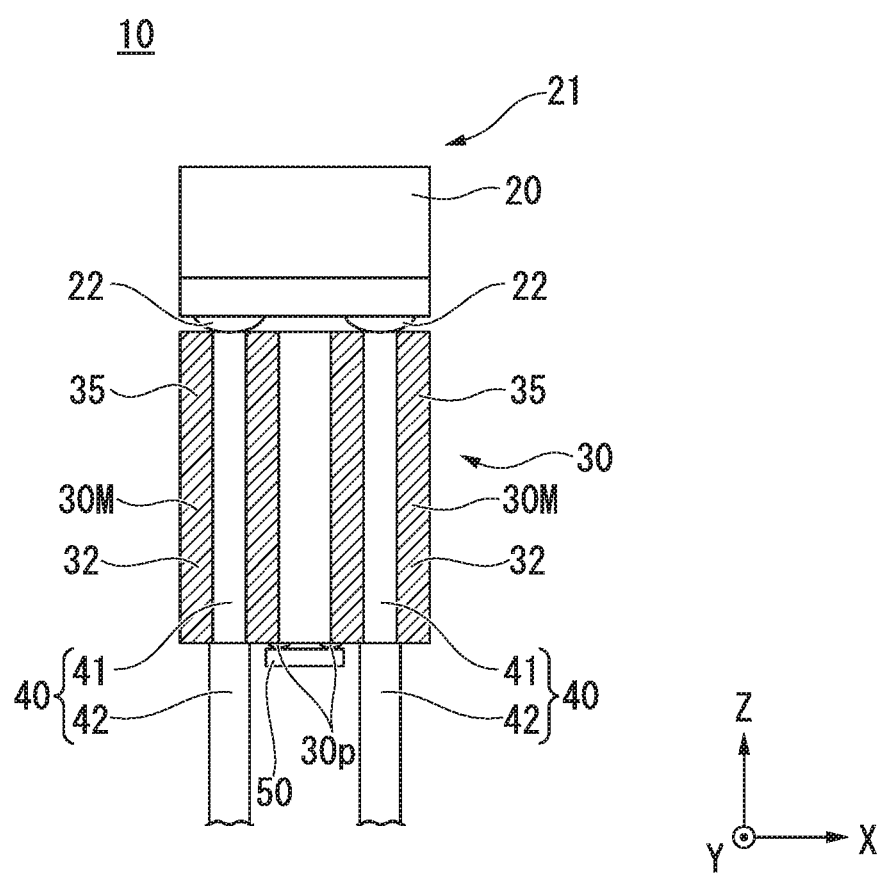
FIG. 5 is a side view showing the configuration of an imaging module according to a second embodiment of the invention.

FIG. 5 is a side view showing the configuration of an imaging module 10 according to a second embodiment of the invention.

Figure 6:
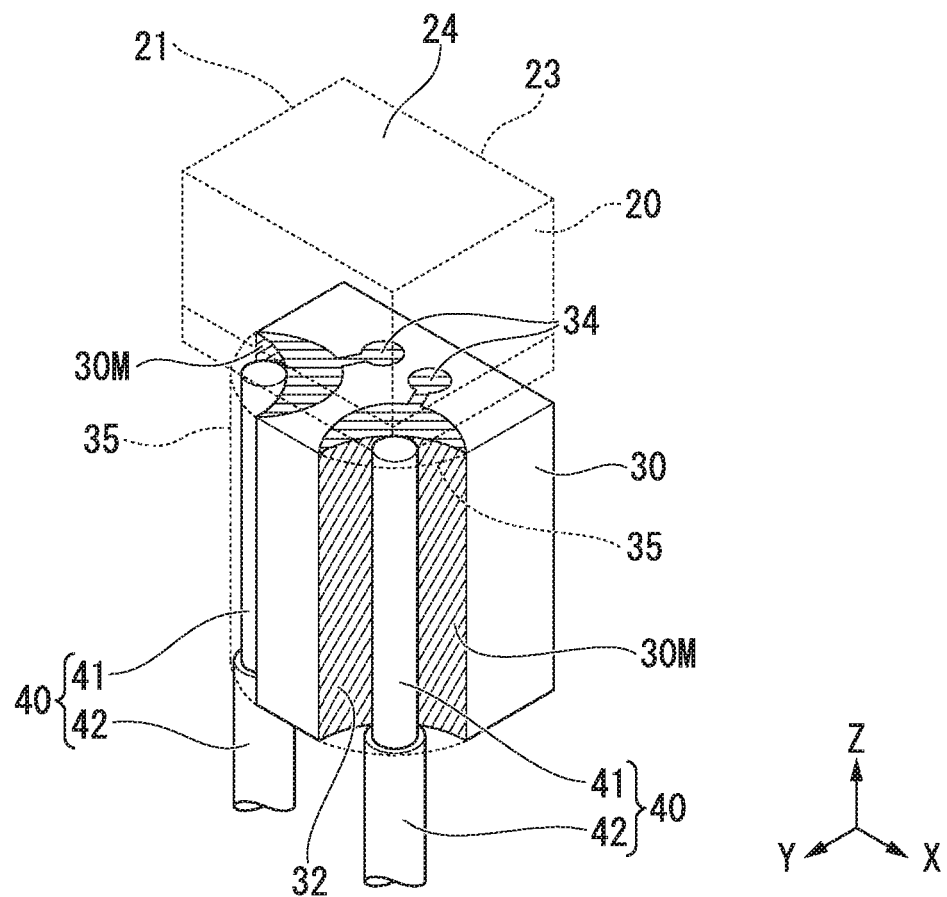
FIG. 6 is a perspective view showing the configuration of the imaging module according to the second embodiment of the invention.

FIG. 6 is a perspective view showing the configuration of the imaging module according to the second embodiment of the invention.

In the second embodiment, identical reference numerals are used for the elements which are identical to those of the first embodiment, and explanations thereof are omitted or simplified here.

The imaging module 10 includes: the solid-state image sensing device 20; a connector 30; and the two signal cables 40 (first signal cable, second signal cable).

In the imaging module 10, the solid-state image sensing device 20 is electrically connected to the two signal cables 40 through the connector 30.

Figure 9:
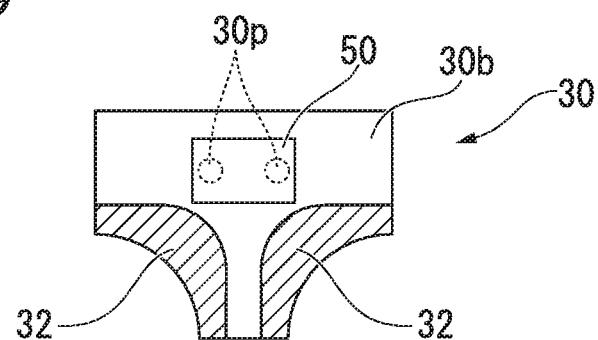
FIG. 9 is a bottom view showing the connector that constitutes the imaging module according to the second embodiment of the invention.

As shown in FIGS. 5 and 9 (which will be described below), the imaging module 10 includes the capacitor 50 (electronic component).

Regarding the configuration of the solid-state image sensing device 20, the configuration of the solid-state image sensing device 20 is the same as that of the above-mentioned first embodiment with the exception that the imaging-device terminals 22 are connected to mounting pads 34 provided on an upper surface 30t of the connector 30.

Figure 7:
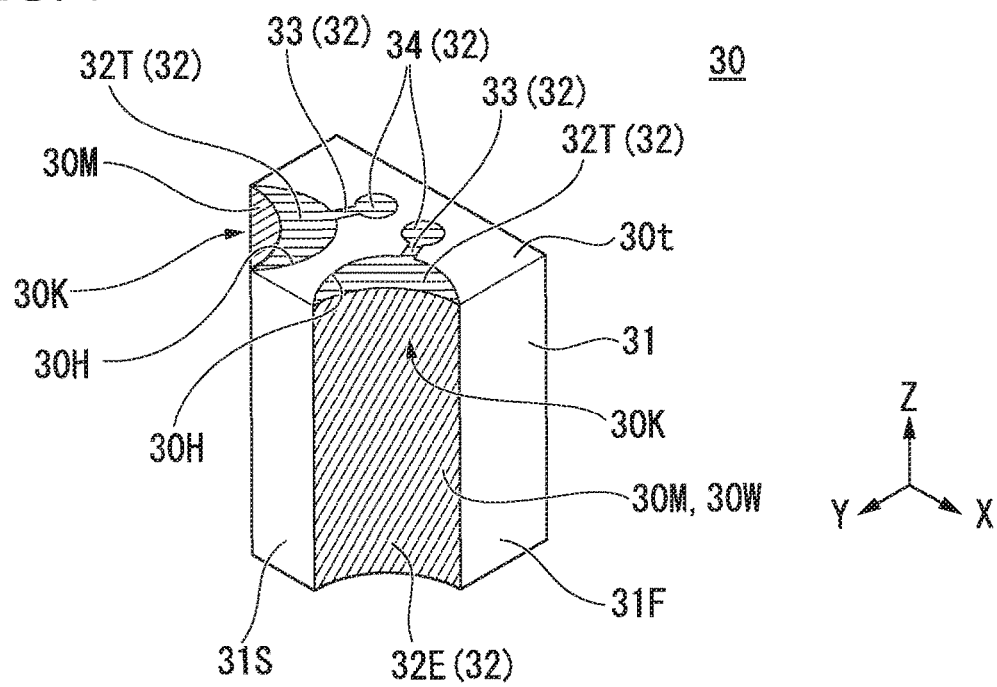
FIG. 7 is a perspective view showing a connector that constitutes the imaging module according to the second embodiment of the invention.
Figure 8:
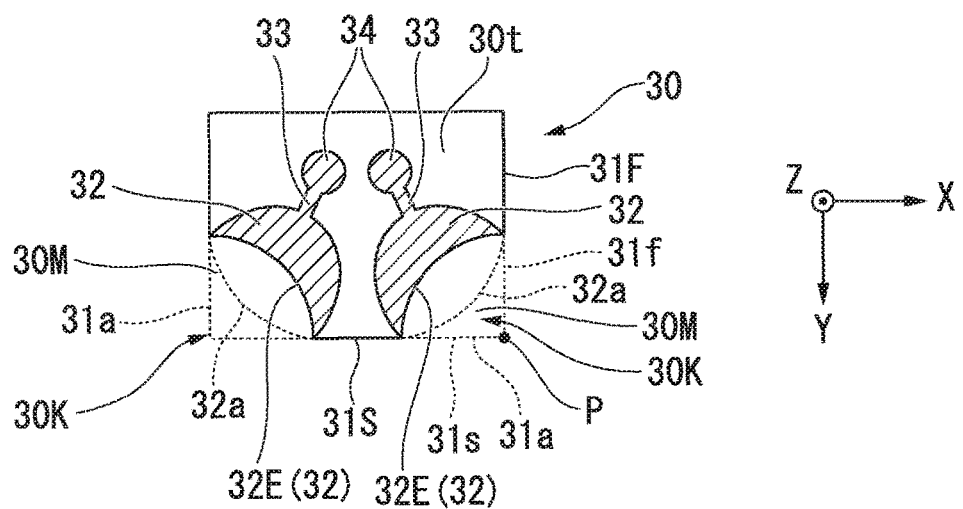
FIG. 8 is a top view showing the connector that constitutes the imaging module according to the second embodiment of the invention.

FIG. 7 is a perspective view showing the connector 30.
FIG. 8 is a top view showing the connector 30.
FIG. 9 is a bottom view showing the connector 30.

In FIG. 8, the length of one side of the connector 30 the X-direction and the Y-direction) is less than or equal to 1 mm.

The connector 30 includes: a main body 31 that functions as an insulator (insulating member); two implanted terminals 32E (second mounting terminal, first implanted terminal, second implanted terminal); two upper surface exposed portions 32T (first upper surface exposed portion, second upper surface exposed portion); two upper wirings 33 (first upper wiring, second upper wiring); two mounting pads 34 (first mounting terminal, first mounting pad, second mounting pad); two implanted conductors 32 (first implanted conductor, second implanted conductor); and mounting pads 30p (fourth mounting terminal).

The main body 31 has the upper surface 30t (first end face); a lower surface 30b (second end face) that is located on the opposite side of the upper surface 30t; a first side face 31F; and a second side face 31S. The first side face 31F and the second side face 31S are orthogonal to the upper surface 30t.

Through holes 30H that penetrate through the main body 31 in the Z-direction, that is, in the direction from the lower surface 30b to the upper surface 30t (first end face) are provided inside the main body 31.

The implanted conductors 32 are implanted in the through holes 30H, and the implanted conductors 32 extend in the Z-direction, that is, in the direction from the lower surface 30b to the upper surface 30t.

That is, the implanted conductors 32 are provided inside the main body 31.

The same material as that of the main body 3A according to the aforementioned first embodiment is adopted as a material used to form the main body 31.

The explanation regarding the material of the main body 31 is omitted in the embodiment.

Each implanted conductor 32 integrally forms the planted terminal 32E, the upper surface exposed portion 32T, the upper wiring 33, and the mounting pad 34.

In other words, the implanted terminal 32E constitutes part of the implanted conductor 32, the upper surface exposed portion 32T constitutes part of the implanted conductor 32, the upper wiring 33 constitutes part of the implanted conductor 32, and the mounting pad 34 constitutes part of the implanted conductor 32.

Regarding the cross-sectional surface parallel to the Z-direction, the cross-sectional configurations of the implanted terminals 32E, the upper surface exposed portion 32T, the upper wirings 33, and the mounting pads 34 which constitute the implanted conductors 32 are the same as those of the configuration shown in FIG. 2.

Specifically, in the case of applying the embodiment to the configuration shown in FIG. 2, reference numeral 6 shown in FIG. 2 corresponds to the implanted conductor according o the embodiment, reference numeral 5 shown in FIG. 2 corresponds to the upper surface exposed portion according to the embodiment, reference numeral 5a shown in FIG. 2 corresponds to the upper wiring according to the embodiment, and reference numeral 5b shown in FIG. 2 corresponds to the mounting pad according to the embodiment.

That is, the implanted conductor 32 includes: the implanted terminals 32E that linearly extend in the Z-direction, and the upper surface exposed portions 32T, the upper wirings 33, and the mounting pads 34 which extend in the direction orthogonal to the implanted terminals 32E. The implanted conductor is formed in an inverted L-shape.

The same material as that of the implanted conductor 6 according to the aforementioned first embodiment is adopted as a material used to form the implanted conductor 32.

The explanation regarding the material of the main body 31 is omitted in the embodiment.

As shown in FIG. 8, the upper surface exposed portions 32T, the upper wirings 33, and the mounting pads 34 are provided on the upper surface 30t and exposed at the upper surface 30t.

The upper wiring 33 is provided between the upper surface exposed portion 32T and the mounting pads 34.

In the example shown in FIG. 8, the width of the upper wiring 33 is smaller than the diameter of the mounting pad 34; however, the invention is not limited to this.

For example, the width of the upper wiring 33 may be larger than the diameter of the mounting pad 34.

The width of the upper surface exposed portion 32T may be gradually smaller in the direction from the upper surface exposed portion 32T to the mounting pad 34.

That is, the invention is not limited to the conductive pattern which is constituted of the upper surface exposed portions 32T, the upper wirings 33, and the mounting pads 34.

The conductive pattern may be a conductive pattern having the portions at which the upper surface exposed portion 32T, the upper wiring 33, and the mounting pad 34 are formed There the portions are not separated from each other. That is, the conductive pattern may be a conductive pattern having the aforementioned portions which are integrated into the pattern.

For example, the conductive pattern may be formed in a fan shape such that the width of the pattern gradually expand in the direction from the mounting pad 34 to the upper surface exposed portion 32T.

The above-mentioned conductive pattern formed on the upper surface 30t as the pattern corresponding to the design of the solid-state image sensing device 20 (arrangement of the imaging-device terminals 22) such that the imaging-device terminals 22 overlap the mounting pads 34 when seen in a plan view (a plan view as seen in the Z-direction).

By means of this structure, when the solid-state image sensing device 20 is mounted on the upper surface 30t, the imaging-device terminals 22 are electrically connected to the ting pads 34.

That is, the mounting pad 34 is electrically connected to the imaging-device terminal 22 and the implanted conductor 32.

In the configuration shown in FIGS. 6 to 8, the upper wirings 33 and the mounting pads 34 are implanted in the main body 31; however, the invention is not limited to this configuration, For example, the upper wiring 33 may be formed on the upper surface 30t of the main body 31 by use of a method such as a printing method so as to electrically connect the upper surface exposed portion 32T and the mounting pad 34.

Particularly, the upper wiring 33 may be a thin-film wiring that is patterned on the upper surface 30t (relocation wiring, a thin film having a wiring pattern).

In this case, a relocation wiring that connects the forming portion of the mounting pad 34 corresponding to the position of the imaging-device terminal 22 and the upper surface exposed portion 32T is formed on the upper surface 30t.

Similarly, the mounting pads 34 may be formed on the upper surface 30t of the main body 31 by use of a method such as a printing method.

That is, the mounting pad 34 may be a thin-film pad that is patterned on the upper surface 30t.

Particularly, as compared with the case where part of the implanted conductor that extends in the Z-direction is a mounting pad (i.e., the case where part of the implanted conductor is exposed at the upper surface 30t), in the case of forming the mounting pads on the upper surface 30t by patterning using, for example, a printing method, the diameter or the width of the mounting pad can easily coincide with the diameter of the imaging-device terminal 22.

Similar to the implanted conductor 32, the implanted terminals 32E extend in the direction, that is, in the direction from the upper surface 30t to the lower surface 30b.

The implanted terminal 32E is exposed to the internal space of the groove 30M provided on the connector 30 (which will be described below).

The signal cable 40 is electrically connected to the implanted terminal 32E.

As described above, the implanted conductor 32 that constitutes the implanted terminal 32E is previously provided inside the connector 30, the groove 30M is formed at the connector 30 by removing (grinding) the corner region 30K of the connector 30, and the implanted terminal 32E is thereby exposed to the inside of the groove 30M.

The implanted terminals 32E will be particularly described with reference to FIG. 8.

In FIG. 8, the dotted line 32a shows the outer shape of the implanted conductors 32 in the corner regions 30K before the corner regions 30K are removed.

The dotted line 31a shows the outer shape of the connector 30 at the corner regions 30K in the corner regions 30K before the corner regions 30K are removed.

That is, in a state before the corner regions 30K are removed, the implanted conductors 32 are provided in the inside of the connector 30 at the corner regions 30K.

Here, as a result of grinding the corner regions 30K, that is, as a result of removing the portions indicated by the dotted lines 31a and 32a, the grooves 30M are formed at the positions corresponding to the corner regions 30K, and parts of the implanted conductors 32 are simultaneously removed.

Consequently, the implanted terminals 32E are exposed to the inside of grooves 30M.

In other words, in a state before the signal cable 40 is connected to the implanted terminal 32E, the implanted terminal 32E can be referred to as an exposed terminal at which part of the implanted conductor 32 is exposed.

As a result of grinding the corner region 30K, a wall surface 30W is formed in the groove 30M.

The wall surface 30W is a grinding surface formed by grinding and can be said to be a surface having a grinding trace that occurs due to contact between a grinding tool and the main body 31.

Since the aforementioned implanted terminal 32E constitutes part of the implanted conductor 32 that is implanted in the main body 31, the implanted terminal 32E has a structure which is completely different from that of the coated film formed on a substrate surface by use of a publicly known film formation method.

Next, the grooves 30M will be particularly described.

In the embodiment, a plurality of the grooves 30M are provided on the connector 30.

Particularly, in the embodiment, the number of the grooves 30M is two.

The main body 31 has the first side face 31F (surface vertical to the X-direction) and the second side face 31S (surface vertical to the Y-direction).

The first side face 31F and the second side face 31S are the surfaces orthogonal to the upper surface 30t of the connector 30 (surface vertical to the Z-direction).

Each groove 30M is provided between the first side face 31F and the second side face 31S.

As indicated by the dotted line shown in FIG. 8, the first virtual extension surface 31f of the first side face 31F (the first virtual extension surface 31f coincides with the first side face 31F on the same plane) intersects with the second virtual extension surface 31s of the second side face 31S (the second virtual extension surface 31s coincides with the second side face 31S on the same plane) at the intersection P.

That is, the space (region) surrounded by the wall surface 30W of the groove 30M, the first virtual extension surface 31f, and the second virtual extension surface 31s corresponds to the groove 30M.

As described below, the signal cable 40 is located inside the grooves 30M, the implanted terminal 32E is electrically connected to the signal cable 40.

The surface of the wall surface 30W, that is, the surface of the implanted terminal 32E is exposed to the inside of the groove 30M and has a curved surface corresponding to the shape of the grinding tool.

As shown in FIG. 7, the implanted terminals 32E are formed on all of curved surfaces formed by removing the corner regions 30K.

The invention is not limited to the implanted terminals 32E shown in FIG. 7.

The implanted terminal 32E may be formed on part of the curved surfaces formed by removing the corner regions 30K.

As shown in FIGS. 5 and 6, the signal cables 40 are arranged at the positions of the grooves 30M.

The conductor 41 extends parallel to the implanted terminal 32E inside the grooves 30M and is connected to the implanted terminal 32E.

Furthermore, the solder 35 is provided so as to coat the conductor 41 and the implanted terminal 32E.

That is, the conductor 41 is soldered to the implanted terminal 32E, and the conductor 41 and the implanted terminal 32E are electrically connected to each other.

The conductor 41, the implanted terminal 32E, and the solder 35 constitute an electrically connected portion.

As shown in FIG. 9, the mounting pads 30p (fourth mounting terminal) are provided on the lower surface 30b of the connector 30.

In a state where the capacitor 50 is mounted on the lower surface 30b of the connector 30, the terminals (electrode) of the capacitor 50 are connected to the mounting pads 30p via solder, the capacitor 50 is electrically connected to the connector 30.

In FIG. 9, the implanted terminals 32E are exposed at the lower surface 30b.

The implanted terminals 32E formed on the lower surface 30b correspond to the end portions of the implanted terminals 32E that extend in the Z-direction (refer to FIG. 7).

In the embodiment, the implanted terminals 32E are arranged separately from the mounting pads 30p; however, wirings, electrodes, terminals, or the like which electrically connect the implanted terminals 32E and the mounting pads 30p may be formed on the lower surface 30b.

In this case, it is possible to electrically connect the solid-state image sensing device 20, the capacitor 50, and the signal cables 40 through the mounting pads 34, the implanted terminals 32E, and the mounting pads 30p which are provided on the connector 30.

Next, a connection structure between the signal cable 40 and the implanted terminal 32E will be described with reference to FIG. 10.

Figure 10:
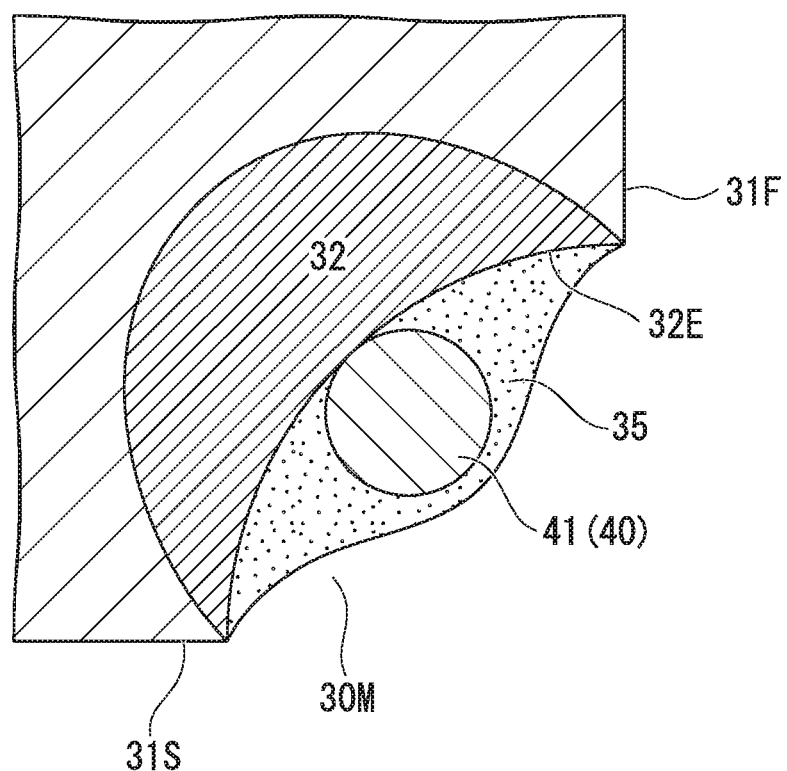
FIG. 10 is a partial cross-sectional view showing a state where a side face exposed portion is connected to a conductor of a signal cable by solder in the connector that constitutes the imaging module according to the second embodiment of the invention.

FIG. 10 is a partial cross-sectional view showing a state where the implanted. terminal 32F is connected to the conductor 41 of the signal cable 40 by the solder 35.

As shown in FIG. 10, the implanted terminal 32E is used as a mount surface, and the signal cable 40 is mounted on this mount surface.

The solder 35 is formed so as to coat the conductor 41 and the implanted terminal 32E in a state of connecting the conductor 41 and the implanted terminal 32E.

Particularly, since the implanted terminal 32E has a curved surface, the signal cable 40 supported by the curved surface of the implanted terminal 32E, it is possible to easily fix the position of the signal cable 40 when the signal cable 40 is arranged on the implanted terminal 32E.

Also, since the solder 35 stays on the curved surface of the implanted terminal 32E when the conductor 41 and the implanted terminal 32E are soldered, it is possible to prevent the solder 35 from flowing to the outside of the main body 31.

That is, the implanted terminal 32E having the curved surface functions as a solder receiver.

Since a method of forming the connector 30 including the above-described implanted terminals 32E is the same as that of the connector 3 according to the first embodiment, the explanation therefor is omitted.

Additionally, in the imaging module 10 according to the second embodiment, similar to the above-mentioned first embodiment, as seen in the vertical direction of the light-receiving face 21, that is, in the direction from the solid-state image sensing device 20 to the lower surface 30b, the connector 30 and the signal cables 40 are located within the region 24 surrounded by the external outline 23 of the solid-state image sensing device 20 (refer to FIG. 6).

According to the imaging module 10 of the above-described embodiment, the same effect as that of the imaging mod is obtained.

Furthermore, since the connector 30 has the grooves 30M, it is possible to easily carry out the positioning of the signal cables 40 with respect to the connector 30.

(Modified Example 1 of Imaging Module)

Figure 11:
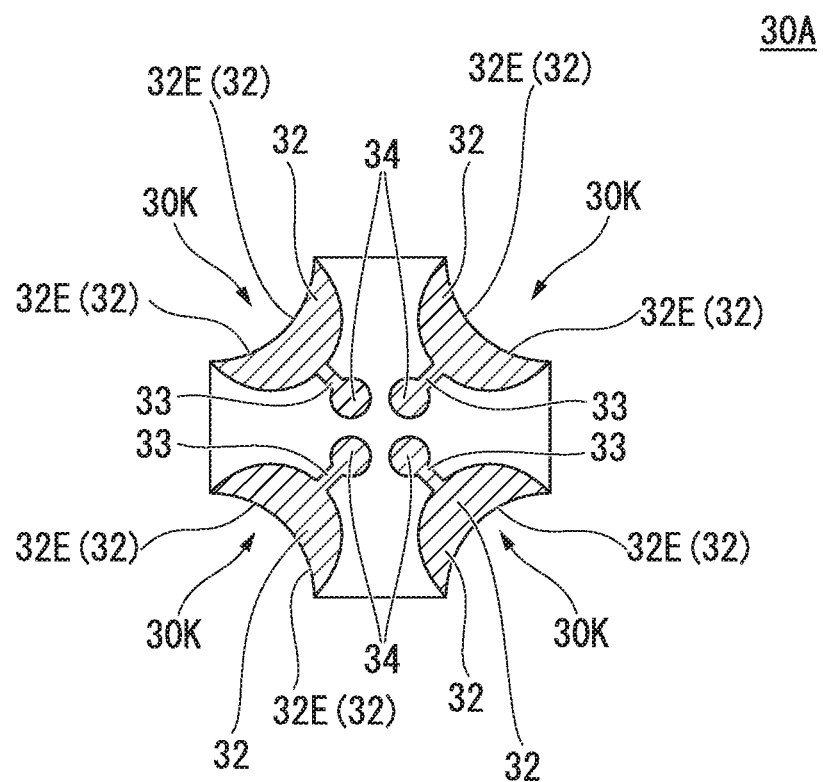
FIG. 11 is a top view showing a connector that constitutes an imaging module according to a modified example 1 of the embodiment of the invention.

FIG. 11 is a top view showing the configuration of a connector that constitutes an imaging module according to a modified example 1 of the embodiment of the invention.

In FIG. 11, identical reference numerals are used for the elements which are identical to those of the above-described embodiments, and explanations thereof are omitted or simplified here.

In the modified example 1, a plurality of grooves 30M are provided on connector 30A Particularly, in the modified example 1, the number of the grooves 30M is four.

The four grooves 30M are located so as to correspond to the four corner regions 30K.

The implanted terminal 32E is exposed to the inside of the groove 30M.

The four implanted terminals 32E are provided in the respective grooves 30M and are disposed at the positions which are opposed to each other.

Specifically, the connector 30A is provided with the four implanted terminals 32E which are formed by grinding the four corner regions 30K.

That is, the implanted terminals 32E according to the modified example 1 are located at the corner regions 30K of the connector 30A and at the positions which are opposed to each other (on the diagonal line).

The configuration of each implanted terminal 32E is the same as that of the above-described embodiment.

The conductor 41 of the signal cable 40 is electrically connected to each of the four implanted terminals 32E.

Consequently, according to the imaging module of the modified example 1, it is possible to electrically connect the signal cable 40, whose number is greater than that of the above-mentioned imaging module 10, to the solid-state image sensing device 20 in addition to the above-described effects.

Even where the number of the signal cables 40 increases, it contributes to reduce the size of the imaging module.

(Modified Example 2 of Imaging Module)

Figure 12:
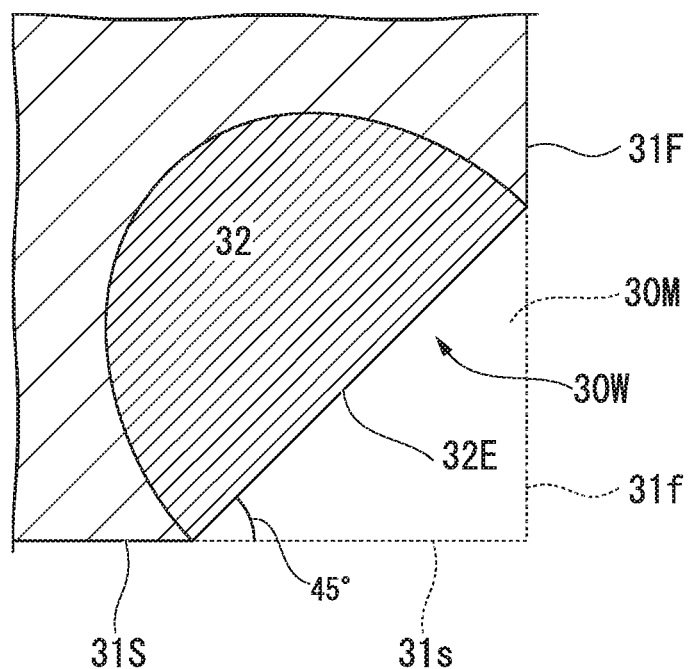
FIG. 12 is a top v showing connector that constitutes an imaging module according to a modified example 2 of the embodiment of the invention.

FIG. 12 is a top view showing the configuration of a connector that constitutes an imaging module according to a modified example 2 of the embodiment of the invention.

FIG. 12, identical reference numerals are used for the elements which are identical to those of the above-described embodiments, and explanations thereof are omitted or simplified here.

In the above-described embodiment, the implanted terminal 32E (the wall surface 30W) which is formed by grinding the connector 30 has a curved surface in the groove 30M.

In the modified example 2, the implanted terminal 32E formed in the groove 30M has an inclined surface (flat surface) that is formed so as to extend in a direction from the first side face 31F to the second side face 31S.

The angle of the inclined surface is 45 degrees.

Even in the case of adopting this configuration to the implanted terminal, it is possible to reliably expose the implanted terminal 32E to the inside of the groove 30M of the main body 31, and the implanted terminal 32E can serve as a mounting terminal.

(Modified Example 3 of Imaging Module)

Figure 13:
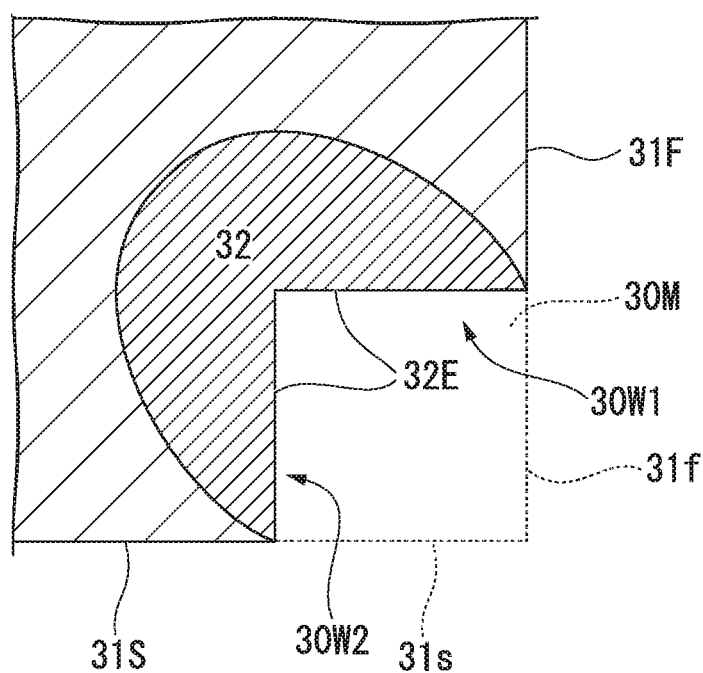
FIG. 13 is a top view shoeing a connector that constitutes an imaging module according a modified example 3 of the embodiment of the invention.

FIG. 13 is a top view showing the configuration of a connector that constitutes an imaging module according to a modified example 3 of the embodiment of the invention.

In FIG. 13, identical reference numerals are used for be elements which are identical to those of the above-described embodiments, and explanations thereof are omitted or simplified here.

In the modified example 3, a first vertical wall surface 30W1 perpendicular to the first side face 31F and a second vertical wall surface 30W2 perpendicular to the second side face 31S are formed in the wall surface 30W.

The implanted terminal 32E is exposed to the inside of the groove 30M including the first vertical wall surface 30W1 and the second vertical wall surface 30W2.

Accordingly, it is possible to reliably expose the implanted terminal 32E in the groove 30M, the implanted terminal 32E, and the implanted terminal 32E can serve as a mounting terminal.

Since the first vertical wall surface 30W1 and the second vertical wall surface 30W2 which form the implanted terminal 32E are orthogonal to each other, the surfaces function as a solder receiver that receives flowing solder.

Consequently, according to the modified example 3, in addition to the effects described in the above-described embodiment, it is possible to prevent the solder from flowing to the outside of the main body 31.

(Modified Example 4 of Imaging Module)

Figure 14:
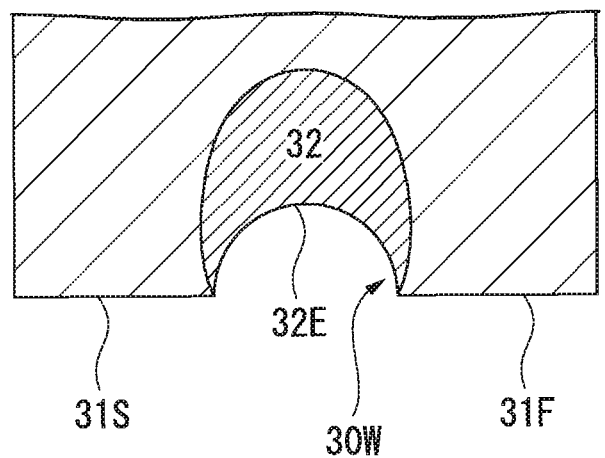
FIG. 14 is a top view showing a connector that constitutes an imaging module according to a modified example 4 of the embodiment of the invention.

FIG. 14 is a top view showing the configuration of a connector that constitutes or an imaging module according to a modified example 4 of the embodiment of the invention.

In FIG. 14, identical reference numerals are used for the elements which are identical to those of the above-described embodiments, and explanations thereof are omitted or simplified here.

In the above-described embodiments and modified examples 1 to 3, the case is described where the second side face 31S orthogonal to the first side face 31F.

The invention is not limited to the embodiments and modified examples. As shown in FIG. 14, the first side face 31F and the second side face 31S may be on the same plane.

Even in this case, the grooves 30M is provided between the first side face 31F and the second side face 31S.

In other cases, it is not necessary that the first side face 31F and the second side face 31S are located on the same plane.

Two side faces may be located parallel to each other so that the positions of the first side face 31F and the second side face 31S are separated from each other in the direction orthogonal to the first side face 31F and the second side face 31S.

The angle formed between the first side face 31F and the second side face 31S may be an acute angle.

(Modified Example 5 of Imaging Module)

Figure 15:
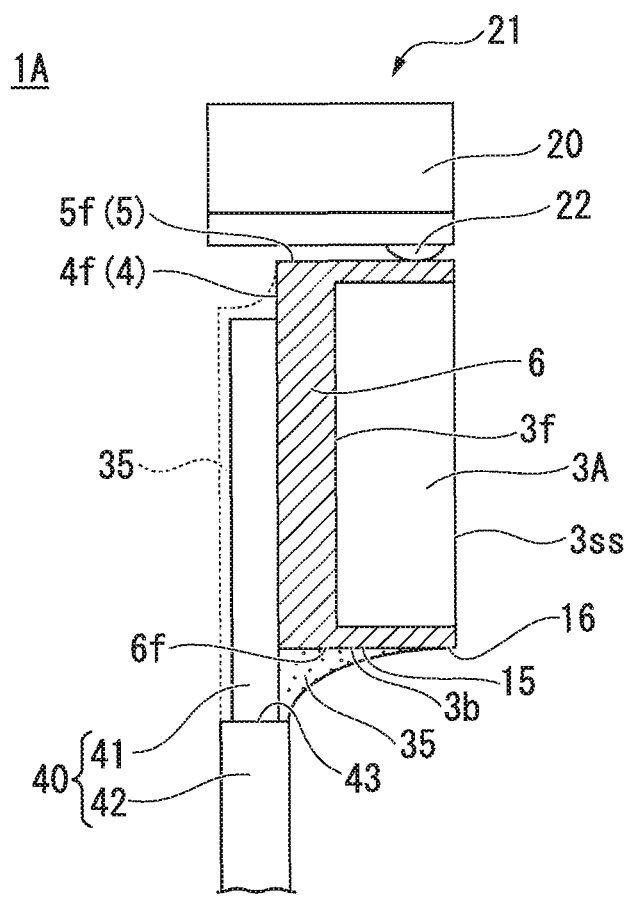
FIG. 15 is a cross-sectional view showing an imaging module according to a modified example 5 of the embodiment of the invention.

FIG. 15 is a cross-sectional view showing an imaging module according to a modified example 5 of the embodiment of the invention.

In FIG. 15, identical reference numerals are used for the elements which are identical to those of the above-described embodiments, and explanations thereof are omitted or simplified here.

The modified example 5 is different from the imaging module 1 according to the first embodiment that a fillet-forming terminal 15 (third mounting terminal) is provided on the lower surface 3b of the connector 3.

Specifically as shown in FIG. 15, in the connector 3 of the imaging module 1A according to the modified example 5, the fillet-forming terminal 15 provided on the lower face 3b is connected to the end of the implanted terminal 4 on the lower surface 3b and constitutes part of the implanted conductor 6.

That is, the implanted conductor 6 integrally forms the implanted terminal 4, the mounting pad 5, and the fillet-forming terminal 15.

The fillet-forming terminal 15 includes a terminal-front-end portion 16.

The terminal-front-end portion 16 is located at the position separated from the connection surface between the implanted terminal 4 and the conductor 41 of the signal cable 40.

In the example shown in FIG. 15, the terminal-front-end portion 16 is the end portion of the fillet-forming terminal 15 located at the boundary between the side face 3ss of the connector 3 (the side face on the opposite side of the side face 3s on which the implanted terminal 4 is provided) and the fillet-forming terminal 15.

The solder 35 is formed on the lower surface 3b so as to coat the fillet-forming terminal 15 and the implanted terminal 4.

The signal cable 40 has a cable boundary portion 43 located at the boundary between the conductor 41 and the coated portion 42.

The cable boundary portion 43 is located outside the lower surface 3b, that is, located at the position apart from the lower surface 3b.

The solder 35 electrically connects the fillet-forming terminal 5 and the conductor 41.

In particular, the solder 35 coats the fillet-forming terminal 15 and the conductor 41 so as to forma curved surface that extends from the terminal-front-end portion 16 to the cable boundary portion 43.

According to the aforementioned modified example 5, the same effects as those of the imaging module 1 according to the first embodiment are obtained.

Since it is possible to not only electrically connect the implanted terminal 4 and the conductor 41 but also electrically connect the fillet-forming terminal 15 and the conductor 41 by the solder s possible to improve the reliability of electrical connection therebetween.

As shown in FIG. 15, the solder 35 is formed along the surface shape of the fillet-forming terminal 15 and the conductor 41, and the cross-sectional shape of the solder 35 is thereby formed in an L shape.

Specifically, the solder 35 connects the fillet-forming terminal 15 and the conductor 41 so as to form the three-dimensional connection structure that expands from the conductor 41 to the entire surface of the fillet-forming terminal 15.

Since the solder 35 is in close contact with the portion between the fillet-forming terminal 15 and the conductor 41, it is possible to improve the mechanical strength between the fillet-forming terminal 15 and the conductor 41.

In the example shown in FIG. 15, the mounting pads 3p are not shown; however, the invention is not limited to the example shown in FIG. 15.

Both the mounting pads 3p and the fillet-forming terminals 15 may be provided on the lower surface 3b.

In this ease, common N (terminal, pad, and electrode) which are common to the mounting pads 3p and the fillet-forming terminals 15 are provided on the lower surface 3b.

The common terminals are connected to the implanted terminals 4.

Specifically, since the number of the terminals of the capacitor 50 is two, two independent common terminals are formed on the lower surface 3b, and the two common terminals are each connected to a corresponding one of the two implanted terminals 4.

The common terminals may be the implanted terminals that are implanted in the main body 3A.

In the case where such common terminals are provided on the lower surface 3b, an insulating coating layer may be provided on the common terminals so as to be located between the mounting pad 3p and the fillet-forming terminal 15 and so as to cross two common terminals.

In this case, for example, the insulating coating layer extends in the direction orthogonal to the direction in which the common terminal extends.

(Modified Example 6 of Imaging Module)

Figure 16:
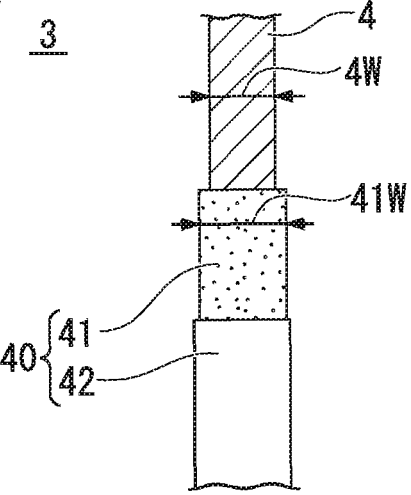
FIG. 16 is an enlarged plan view showing the relevant part of a connector that constitutes an imaging module according to a modified example 6 of the embodiment of the invention.

FIG. 16 is an enlarged plan view showing the relevant part of a connector that constitutes an imaging module according to a modified example 6 of the embodiment of the invention.

In FIG. 16, identical reference numerals are used for the elements which are identical to those of the above-described embodiments, and explanations thereof are omitted or simplified here.

In the above-mentioned first embodiment, as shown in FIG. 1, the structure described in which the conductor 41 having the diameter smaller than the width of the implanted terminal 4 is connected to the implanted terminal 4 on the side face 3s.

The invention is not limited to the ratio of the diameter (diameter in cross-section) of the conductor 41 to the width of the implanted terminal 4.

As shown in FIG. 16, the diameter 41w of the conductor 41 may be larger than the width 4w of the implanted terminal 4.

(Modified Example 7 of Imaging Module)

Figure 17:
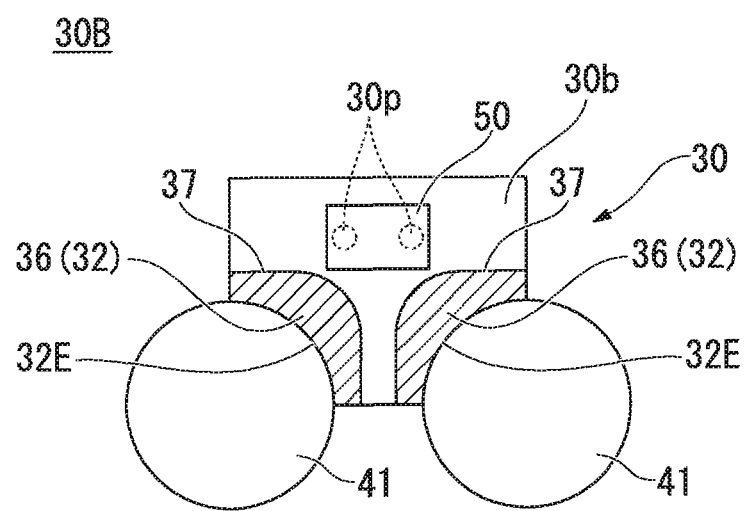
FIG. 17 is a bottom view showing a connector that constitutes an imaging module according to a modified example 7 of the embodiment of the invention.

FIG. 17 is a bottom view showing a connector that constitutes an imaging module according to a modified example 7 of the embodiment of the invention.

Figure 18:
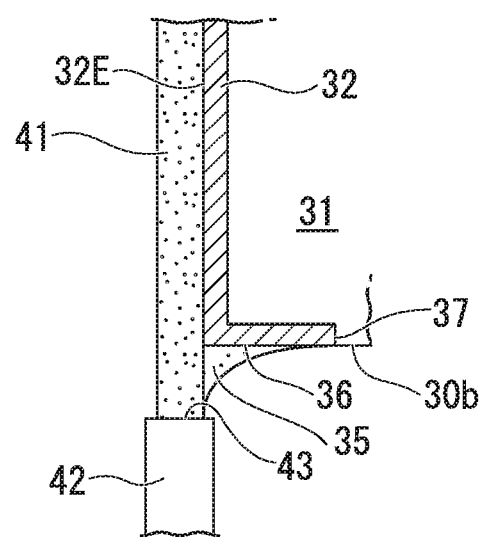
FIG. 18 is an enlarged cross-sectional view showing the relevant part of a connector that constitutes an imaging module according to a modified example 7 of the embodiment of the invention.

FIG. 18 is an enlarged cross-sectional view showing the relevant part of a connector that constitutes an imaging module according to a modified example 7 of the embodiment of the invention.

In FIGS. 17 and 18, identical reference numerals are used for the elements which are identical to those of the above-described embodiments, and explanations thereof are omitted or simplified here.

In the above-mentioned second embodiment, as shown FIG. 10, the structure is described in which the conductor 41 having a diameter smaller than the size of the implanted terminal 32E is arranged inside the groove 30M, that is, the conductor 41 is accommodated in the groove 30M.

The invention not limited to the ratio of the diameter (diameter in cross-section) of the conductor 41 to the size of the implanted terminal 32E.

As shown in FIG. 17, the conductor 41 that is to be connected to the implanted terminal 32E may have a large diameter such that the conductor protrudes from the groove 30M to the outside.

In the case where the diameter of the conductor 41 is larger as described above, the connector 30B according to the modified example 7 is applicable to an imaging module.

The modified example 7 is different from the imaging module 10 according to the second embodiment in that fillet-forming terminal 36 (third mounting terminal) are provided on the lower surface 30b of the connector 30B.

Particularly, as shown in FIG. 17, in the connector 30B according to the modified example 7, the fillet-forming terminals 36 provided on the lower surface 30b are connected to the end portions of the implanted terminals 32E on the lower surface 30b and constitute part of the implanted conductor 32.

That is, each implanted conductor 32 integrally forms the implanted terminal 32E, the upper surface exposed portion 32T, the upper wiring 33, the mounting pad 34, and the fillet-forming terminal 36.

The fillet-forming terminal 36 has a terminal-front-end portion 37.

The terminal-front-end portion 37 is located separately from the connection surface between the implanted terminal 32F and the conductor 41 of the signal cable 40.

In the example shown in FIG. 17, the terminal-front-end portion 37 is located at a substantially center of the connector 30B.

That is, the terminal-front-end portion 37 is not formed on the entire surface of the lower surface 30b.

Specifically, the lower surface 30b has a first mounting region and a second mounting region. On the first mounting region, the mounting pads 30p are formed, and the capacitor 50 is to be mounted on the mounting pads 30p. On second mounting region, the fillet-forming terminals 36 are formed.

In the example shown in FIG. 17, the mounting pads 30p are formed on the region (first mounting region) that is located upper than the terminal-front-end portion 37, and the fillet-forming terminals 36 are formed on the region (second mounting region) that is located lower than the terminal-front-end portion 37.

As shown in FIG. 18, the solder 35 is formed on the lower surface 30b so as to coat the fillet-forming terminal 36 and the implanted terminal 32F.

Similar to the aforementioned modified example 5, the signal cable 40 has the cable boundary portion 43.

The solder 35 electrically connects the fillet-forming terminal 36 and the conductor 41.

In particular, the solder 35 coats the fillet-forming terminal 36 and the conductor 41 so as to firm a curved surface that extends from the terminal-front-end portion 37 to the cable boundary portion 43.

According to the aforementioned modified example 7, the same effects as those of the imaging module 10 according to the second embodiment are obtained.

Since it is possible to not only electrically connect the implanted terminal 32E and the conductor 41 but also electrically connect the fillet-forming terminal 36 and the conductor 41 by the solder 35, it is possible to improve the reliability of electrical connection therebetween.

In the case where the conductor 4l that is to be connected to the implanted terminal 32E has a large, diameter such that the conductor protrudes from the groove 30M to the outside, it is necessary to check a connecting condition between the conductor 41 and the connector 30B.

In this case, by observing the lower surface 30b, it is possible to determine whether or not the solder 35 has fillet configuration (back fillet) on the fillet-forming terminal 36, and it is thereby possible to easily determine a connecting condition between the conductor 41 and the connector 30B.

(Third Embodiment)

Figure 19:
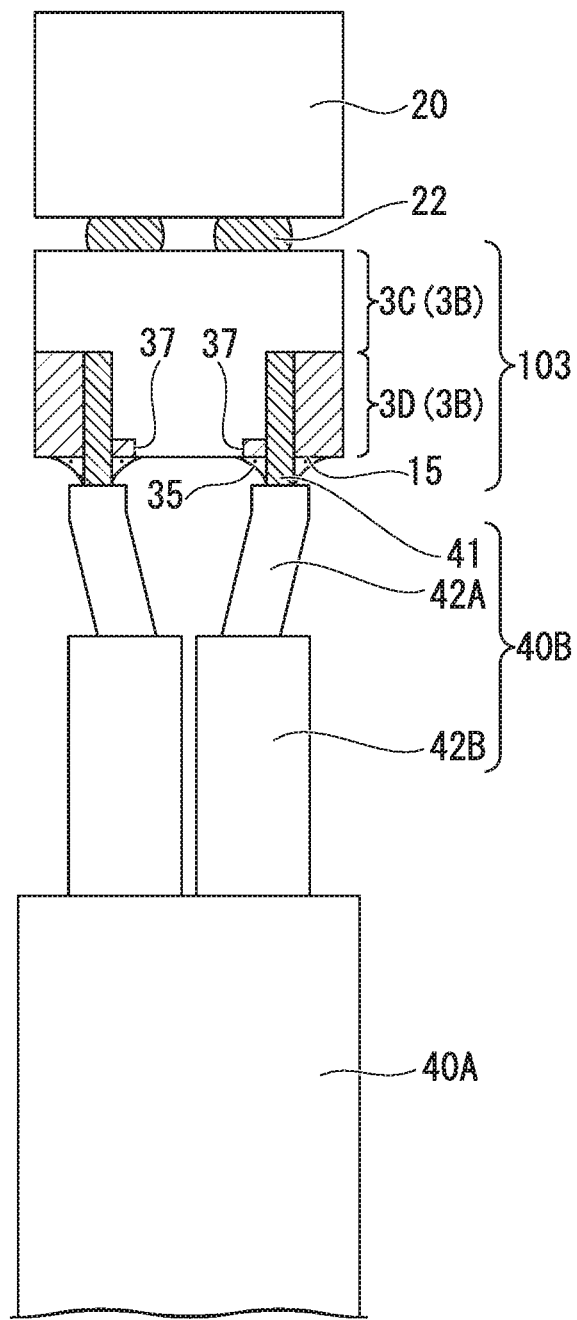
FIG. 19 is a side view showing a configuration of an imaging module according to a third embodiment of the invention.

FIG. 19 is a side view showing a configuration of an imaging module 100 according to the third embodiment.

In the third embodiment, identical reference numerals are used for the elements which are identical to those of the first embodiment, the second embodiment, and the modified examples 1 to 7, and explanations thereof are omitted or simplified here.

The imaging module 100 includes the solid-state image sensing device 20, a connector 103, and a signal cable 40A that collects four wirings 40B (first wiring, second wiring, third wiring, and fourth wiring).

Each wiring 40B includes the conductor 41, a first coated portion 42A that coats the conductor 41, and a second coated portion 42B that coats the first coated portion 42A.

The signal cable 40A is configured to cover the outer-periphery of the four wirings 40B.

A main body 3B (insulating member) that constitutes the connector 103 includes: a conductor penetration region 3C through which the implanted conductor 6 penetrates; and a conductor exposed region 3D in which the groove 30M is formed. In the conductor exposed region 3D, part of the implanted conductor 6 (implanted terminal 32E) is exposed to the groove 30M.

Particularly, in the description, two regions of the connector 103 are referred to as "conductor penetration region 3C" and "conductor exposed region 3D" in order to explain the configuration of the connector 103; however, this does not mean that the connector 103 is separately formed by the two regions.

As described hereinbelow, the conductor penetration region 3C and the conductor exposed region 3D are integrally formed in the connector 103.

The connector 103 has the configuration in which an implanted conductor having a three-dimensional structure is formed inside the main body 3B serving as an insulating member.

More specifically, the implanted conductor 6 is an integrally molded member formed in the connector 103.

Figure 22:
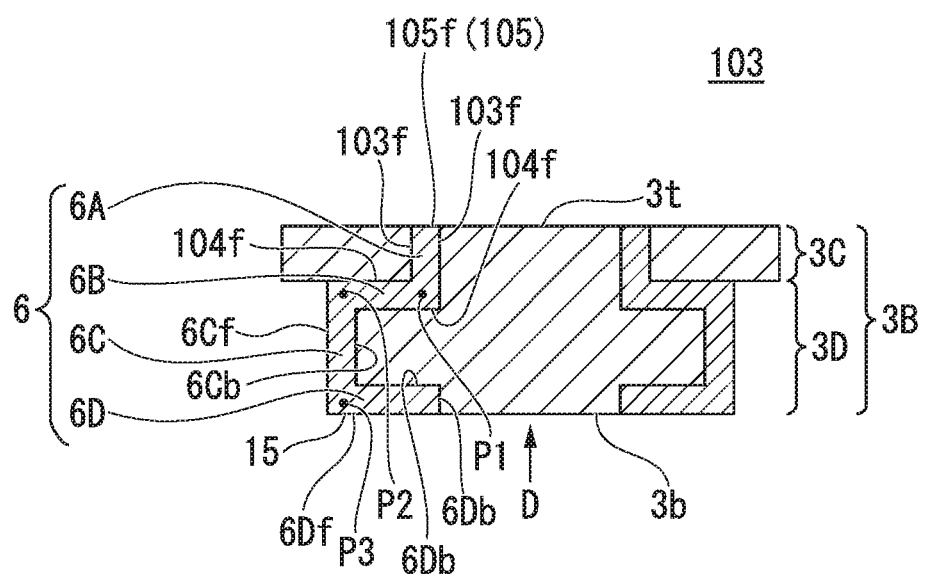
FIG. 22 is an enlarged view showing the connector that constitutes the imaging module according to the third embodiment of the invention and is a cross-sectional view taken along the line B-B shown FIG. 21.

In FIG. 22, the integrally molded member is conductor surrounded by the following surfaces (1) to (7).

(1) top surface 105f of the mounting pad 105;
(2) contact surface 103f that is continuously connected to the surface 105f and is located between an internal conductor 6A and the insulating member (main body 3B);
(3) contact surface 104f that is continuously connected to the contact surface 103f and is located between a connection conductor 6B and the insulating member;
(4) surface 6Cf of a side-surface exposed conductor 6C which is continuously connected to the contact surface 104;
(5) contact surface 6Cb that is located between the side-surface exposed conductor 6C and the insulating member;
(6) surface 6Df of a lower-surface exposed conductor 6D which is continuously connected to the surface 6Cf; and
(7) contact surface 6Db that is located between the lower-surface exposed conductor 6D and the insulating member.

The side view of FIG. 19 shows two wirings 40B; however, other two wirings 40B which are not shown in the figure are arranged at the positions that overlap the two wirings 40B.

The signal cable 40A includes four wirings 40B that correspond to four mounting pads 105 described below with reference to FIG. 21.

In the imaging module 100, the solid-state image sensing device 20 is electrically connected to the four wirings 40B with the connector 103 interposed therebetween.

Figure 20:
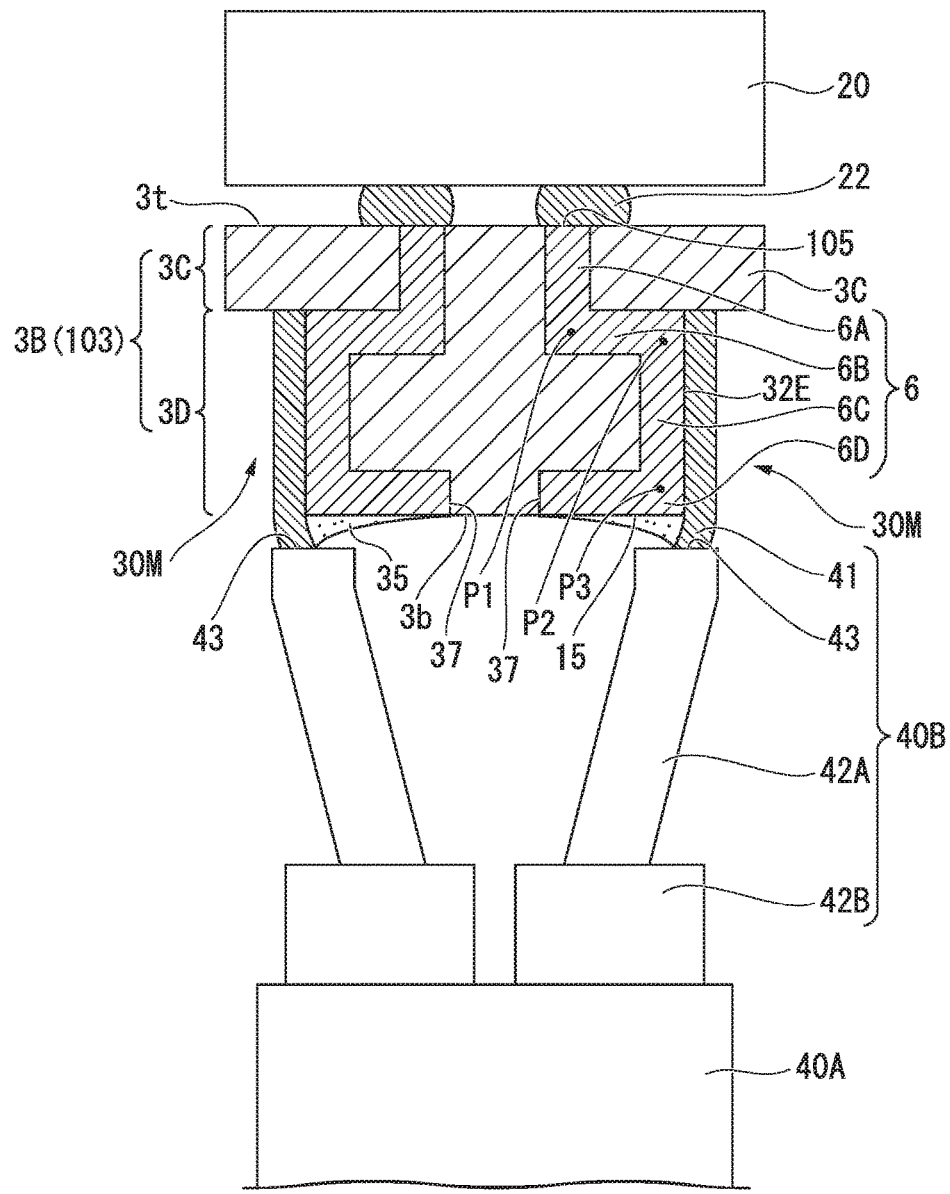
FIG. 20 is an enlarged view showing the configuration of the imaging module according to the third embodiment of the invention and is a cross-sectional view showing a connector that constitutes the imaging module.

FIG. 20 is an enlarged view showing the configuration of the imaging module 100 according to the third embodiment and is a cross-sectional view showing a connector 103 that constitutes the imaging module 100.

Figure 21:
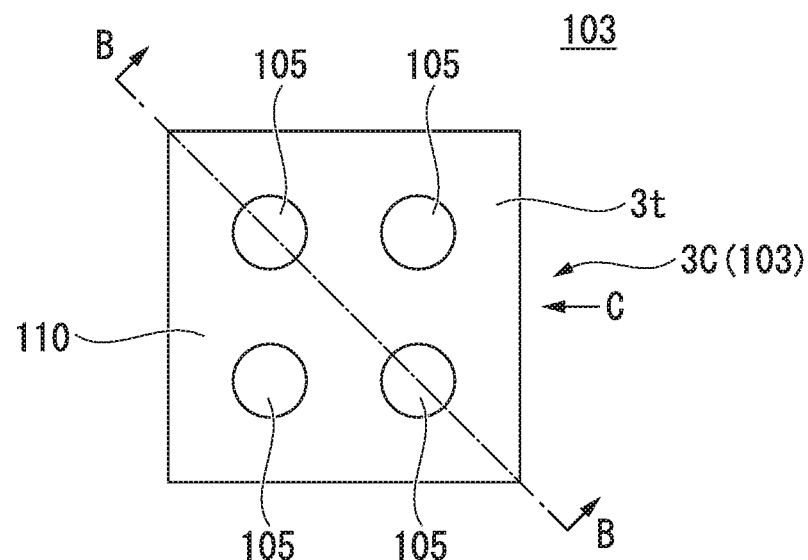
FIG. 21 is a top view showing the connector that constitutes the imaging module according to the third embodiment of the invention.

FIG. 21 is a top view showing the connector 103.

FIG. 22 is an enlarged view showing the connector 103 and is a cross-sectional view taken along the line B-B shown in FIG. 21

Figure 23:
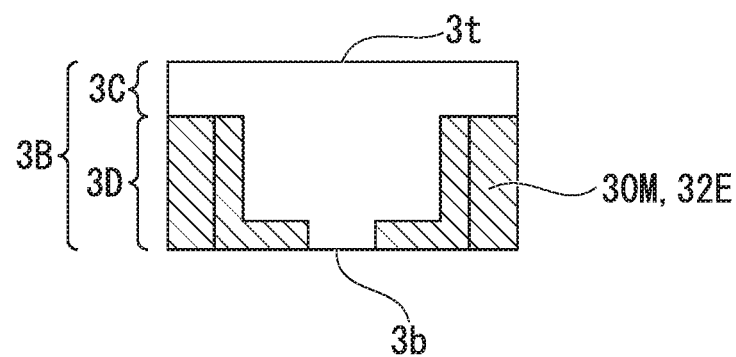
FIG. 23 is an enlarged view showing the connector that constitutes the imaging module according to the third embodiment of the invention and is a side view seen in the direction of the arrow C shown in FIG. 21.

FIG. 23 is an enlarged view showing the connector 103 and is a side view seen in the direction of the arrow C shown in FIG. 21.

Figure 24:
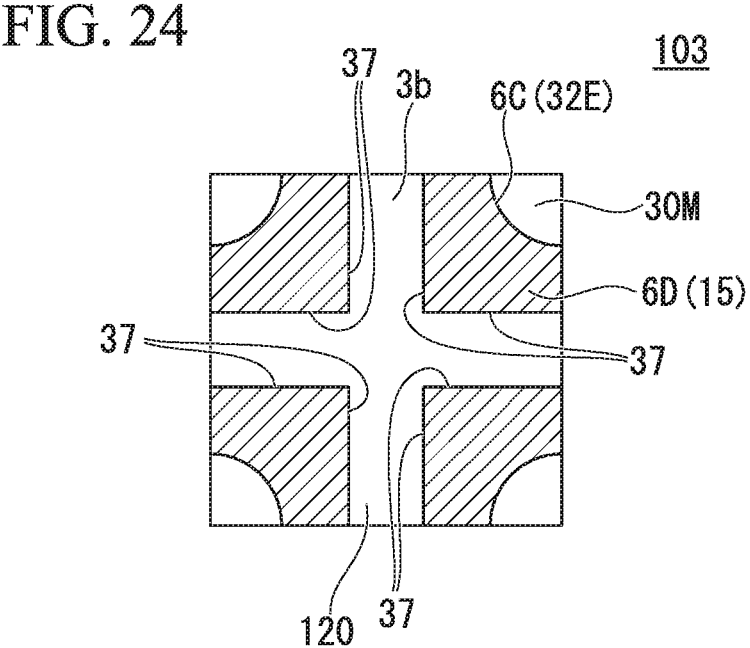
FIG. 24 is an enlarged view showing lie connector that constitutes the imaging module according to the third embodiment of the invention and is a bottom view seen in the direction of the arrow D shown in FIG. 22.

FIG. 24 is an enlarged view showing the connector 103 and is a side view seen in the direction of the arrow D shown in FIG. 22.

Similar to the aforementioned embodiments and the modified examples, the connector 103 includes the implanted conductor 6 provided inside the connector 103.

In the embodiment, four implanted conductors 6 (first implanted conductor, second implanted conductor, third implanted conductor, and fourth implanted conductor) are formed in the connector 103.

Each implanted conductor 6 includes a mounting pad 105 (first mounting terminal), an internal conductor 6A, a connection conductor 6B, a side-surface exposed conductor 6C (second mounting terminal), a lower-surface exposed conductor 6D (third mounting terminal), and the fillet-forming terminal 15.

In the following explanation, each of the internal conductor 6A, the connection conductor 6B, the side-surface exposed conductor 6C, and the lower-surface exposed conductor 6D will be described; however, the conductors 6A, 6B, 6C, and 6D are not separated from each other, are integrally formed in one body, and constitute the implanted conductor 6 having a three-dimensional structure.

As shown in FIG. 21, the mounting pads 105 are provided on the upper surface 3t of the conductor penetration region 3C of the connector 103 and are terminals to be connected to the imaging-device terminals 22.

In the example shown in FIG. 21, each of the mounting pads 105 is formed in a circular shape; however, the shape of the mounting pad 105 is not limited to the circular shape, and other shapes such as a rectangular ape or an elliptical shape may be adopted.

Arrangement of the four mounting pads 105 and a surface area of each pad are appropriately adjusted depending on arrangement of the imaging-device terminals 22, a supply amount of solder (solder paste) that electrically connects the imaging-device terminals 22 and the mounting pads 105, or the like.

On the upper surface it of the conductor penetration region 3C the portion which the mounting pads 105 are not formed is an insulation region (insulator) 110 at which the constituent material of the connector 103 is exposed.

That is, since each of the fur mounting pads 105 is surrounded by the insulation region 110, in the case where solder paste having flowability is applied to the mounting pad 105, the solder paste is prevented from flowing to the outside (insulation region) of the mounting pad 105.

The internal conductor 6A constitutes part of the implanted conductor provided inside the connector 103 so as to penetrate through the conductor penetration region 3C, and extends from h upper surface 3t to the lower face 3b.

One end (upper end) of the internal conductor 6A is the mounting pad 105.

The connection conductor 6B constitutes part of the implanted conductor 6.

The connection conductor 6B extends from the other end (lower end) of the internal conductor 6A toward the outside of the connector 103 in a direction orthogonal to the extending direction of the internal conductor 6A.

In other words, the internal conductor 6A and the connection conductor 6B are connected at the point P1 (inner end) and can be said to form a bent portion.

In the inside of the connector 103, the connection conductor 6B electrically connects the internal conductor 6A and the side-surface exposed conductor 6C.

Particularly, the example shown in FIG. 20, between the conductor penetration region 3C and the conductor exposed region 3D, the connection conductor 6B is located inside the conductor exposed region 3D; however, the invention is not limited to this configuration, The connection conductor 6B may be located inside the conductor penetration region 3C.

The side-surface exposed conductor 6C constitutes part of the implanted conductor 6, is provided on the side surface of the connector 103, and is exposed to the inside of the groove 30M of the conductor exposed region 3D.

The side-surface exposed conductor 6C extends from the outer end of the connection conductor 6B to the lower face 3b of the connector 103 in a direction parallel to the extending direction of the internal conductor 6A.

In other words, the connection conductor 6B and the side-surface exposed conductor 6C are connected at the point P2 (outer end) and can be said to form a bent portion.

The side-surface exposed conductor 6C functions as the implanted terminal 32E which is described in the above-described embodiments and modified examples.

The lower-surface exposed conductor 6D constitutes part of the implanted conductor 6 and is exposed at the lower face 3b of the connector 103. lower-surface exposed conductor 6D extends from the lower end of the side-surface exposed conductor 6C toward the inside of the connector 103 in a direction orthogonal to the extending direction of the side-surface exposed conductor 6C.

In other words, the side-surface exposed conductor 6C and the lower-surface exposed conductor 6D are connected at the point P3 (lower end) and can be said to form a bent portion.

The surface of the lower-surface exposed conductor 6D which is exposed at the lower face 3b functions as the fillet-forming terminal 15 which is described in the above-described embodiments and modified examples.

As shown in FIG. 24, four lower-surface exposed conductors 6D are provided on the lower face 3b.

As shown in FIGS, 18 to 20, each of the four lower-surface exposed conductors 6D has the terminal-front-end portion 37.

The terminal-front-end portion 37 is located separately from the connection surface between the side-surface exposed conductor 6C (implanted terminal 32E) and the conductor 41.

In the example shown in FIG. 24, the terminal-front-end portions 37 are located at a substantially center of the connector 103, and a crisscross pattern surrounded by the terminal-front-end portions 37 of the four lower-surface exposed conductors 6D is formed.

On the lower face 3b, the portion on which the lower-surface exposed conductors 6D are not formed is an insulation region (insulator) 120 at which the constituent material of the connector 103 is exposed.

That is, since each of the four lower-surface exposed conductors 6D is surrounded by the insulation region 120, solder (solder paste) applied to the lower-surface exposed conductor 6D is prevented from flowing to the outside (insulation region) of the lower-surface exposed conductor 6D.

As shown in FIGS. 19 and 20, the solder 35 applied on the lower-surface exposed conductor 6D stays the lower-surface exposed conductor 6D and thereby electrically connects the lower-surface exposed conductor 6D and the conductor 41.

In particular, the solder 35 coats the lower-surface exposed conductor 6D and the conductor 41 so as to form a curved surface that extends from the terminal-front-end portion 37 to the cable boundary portion 43.

Next, a method of forming the connector 103 will be described.

For example, in the case of using a sintered member as the member that constitutes the connector 103, it is believed that the connector 103 is formed by use of the following material and method.

Firstly, by use of a material such as ceramic, an insulating member having a through hole is formed.

Specifically, two insulating members which correspond to the aforementioned conductor penetration region 3C and the conductor exposed region 3D are formed.

The two members have through holes which are formed at a position corresponding to the positions of the implanted conductor 6 shown in FIG. 22.

Next, the through hole of each of the two insulating members is filled with an electroconductive material, a filled via is formed in each insulating member, and therefore two filled vias are formed in the two insulating members.

The formation of the filled vias are not collectively carried out in the two insulating members, and the formation of the filled via is individually carried out in each of two insulating members.

Thereafter, the two members (insulating member) in which the filled vias are formed in the through holes are stacked so as to correspond to the positions of the conductor penetration region 3C and the conductor exposed region 3D (stacking step).

Subsequently, in a sintering step, stacked insulating members (stacked body formed of the two members) in which the filled vias are formed are sintered, and a sintered member is thereby formed.

Next, the corner regions of the sintered member are ground and removed by use of a grinding tool having a diameter larger than the via hole diameter of the filled via (grinding step).

As a result, part of the insulating member and part of filled via of the sintered member are removed, the connector 103 is obtained in which the lower-surface exposed conductor 6D (implanted terminal 32E) is formed.

In the method of forming the aforementioned connector 103, the stacking step, the sintering step, and the grinding step are carried out in this order. However, in other cases, the order of the above steps may be modified.

For example, before carrying out of the sintering step, the grinding step may be carried out.

Before carrying out of the stacking step, the grinding step may be carried out. In the case of carrying out the grinding step before the sintering step, since the insulating member is relatively soft, there is an advantage in that it is possible to easily carry out the grinding step.

In the case of carrying out the grinding step before the stacking step, since the accuracy of position of the grinding tool in the Z-direction is not required, there is an advantage in that the manufacture thereof is easy.

Next, an other method of forming the connector 103 including the above-described implanted terminal 32E will be described.

For example, in the case of using a glass epoxy substrate or a ferrule substrate, which serves as a member constituting be connector 103, it is believed that the connector 103 is formed by use of the following material and method.

Firstly, two insulating members corresponding to the aforementioned conductor penetration region 3C and the conductor exposed region 3D are prepared.

The two insulating members are a glass epoxy substrate or a ferrule substrate.

Next, in each of the two insulating members, a through hole is formed at the position of the implanted conductor 6 shown in FIG. 22.

Furthermore, a filled via is formed in the through hole of each of the two insulating members by a method, such as, for example, plating or the like.

Thereafter, the two members (insulating member) in which the filled vias are formed in the through holes are stacked so as to correspond to the positions of the conductor penetration region 3C and the conductor exposed region 3D (stacking step).

Next, the corner regions of the stacked member are ground and removed by use of a tool having a diameter larger than the diameter of the filled via (grinding step).

As a result, part of the main body 3B and part of the filled via are removed, and the connector 103 is obtained in which the implanted terminal 32F are formed, In other cases, in the method of forming the aforementioned connector 103, before carrying out of the stacking step, the grinding step may be carried out.

In this case, since the accuracy of position of the grinding tool in the-direction is not required, there is an advantage in that the manufacture thereof is easy.

Next, an other method of forming the connector 103 including the above-described implanted terminal 32E will be described.

For example, in the case of using a silicon substrate or a glass substrate, which serves as a member constituting the connector 103, it is believed that the connector 103 is formed by use of the following material and method.

Firstly, two insulating members corresponding to the aforementioned conductor penetration region 3C and the conductor exposed region 3D are prepared.

The two insulating members are a silicon substrate or a glass substrate.

Next, in each of the two insulating members, a through hole is formed at the position of the implanted conductor 6 shown in FIG. 22.

Through-hole interconnections (through silicon via, TSV) are formed in each of through holes of the two insulating members.

Thereafter, two members (insulating member) having through-hole interconnections formed in through holes are stacked so as to correspond to the positions of the conductor penetration region 3C and the conductor exposed region 3D (stacking step).

Next, the corner regions of the stacked member are ground and removed by use of a tool having a diameter larger than the diameter of the through-hole interconnection (grinding step).

As a result, part of the main body 3B and part of the through-hole interconnection are removed, the connector 103 is obtained in which the implanted terminal 32E are formed.

In other cases, in the method of forming the aforementioned connector 103, before carrying out of the stacking step, the grinding step may be carried out.

In this case, since the accuracy of position of the grinding tool in the Z-direction is not required, there is an advantage in that the manufacture thereof is easy.

According to the third embodiment, it is possible to form an implanted conductor having a three-dimensional structure inside the connector 103 in addition to the effect obtained by the above-mentioned embodiments and modified examples.

Furthermore, in a step of mounting the solid-state image sensing device 20 on the connector 103, the imaging-device terminals 22 are connected to the mounting pads 105 via solder paste having flowability. In this case, since the mounting pads 105 are surrounded by the insulation region 110, it is possible to prevent the solder paste from flowing to the outside (insulation region) of the mounting pads 105.

As a result, it is possible to reliably obtain electrical connection between the imaging-device terminals 22 and the mounting pads 105, and it is possible to prevent occurrence of short-circuiting due to flow of solder paste toward the portion other than the mounting pads 105.

While preferred embodiments of the invention have been described and illustrated above, it should be understood that these are exemplary examples of the invention and are not to be considered as limiting. Additions, omissions, substitutions, and other modifications can be made without departing from the scope of the invention, Accordingly, the invention is not to be considered as being limited by the foregoing description, and is only limited by the scope of the appended claims.

For example, an insulating tube may be provided so as to coat the side face of the imaging module according to the above-described embodiments and modified examples, that is, so as to coat the outer side of the connectors 3, 30, 30A, 30B, and the signal cable 40.

In the above-described embodiments and modified examples, the implanted terminals 32E are exposed to the outside by grinding the corner regions 30K of the connector 30 (30A, 30B); however, the corner regions 30K may be removed by polishing the corner regions 30K, and the implanted terminal 32E may be exposed to the outside.

In this case, the wall surface 30W of the groove 30M is a polished surface formed by polishing and can be said to be a surface having a polishing trace that occurs due to contact between a polishing tool and the main body 31.

In the above-described embodiment, as shown in FIG. 8, the structure is described in which the upper wiring 33 is provided between the mounting pad 34 and the upper surface exposed portion 32T on the upper surface 30t.

In the invention, it is not necessarily required to provide the upper wiring 33, the mounting pad 34 may be provided on the top of the upper surface exposed portion 32T on the upper surface 30t, and the implanted terminal 32E may be electrically connected to the solid-state image sensing device 20.

In the above-described embodiments, the case is described where an example of "first end face" of the invention is the upper surface 30t, and an example of "second end face" of the invention is the lower surface 30b.

The invention is not limited to the positions of "first end face" and "second end face".

An example of the first end face may be the lower surface 30b, and an example of the second end face may be the upper surface 30t.

In the case where the imaging module is positioned so that the direction from the first end face to the second end face intersects with the direction of gravitational force, the first end face may be a left end face, and the second end face may be a right end face.

Conversely, the first end face may be a right end face, and the second end face may be a left end face.

What is claimed is:

1. An imaging module comprising:
a solid-state image sensing device comprising an imaging-device terminal;
a connector having a first end face, a second end face located opposite to the first end face, and a side face orthogonal to the first end face, the connector comprising: a main body serving as an insulating member, an implanted conductor that is implanted in an inside of the main body, a first mounting terminal that is electrically connected to the imaging-device terminal and the implanted conductor and is provided on the first end face, a second mounting terminal that is provided on the side face and constitutes part of the implanted conductor, and a third mounting terminal that is provided on the second end face and constitutes part of the implanted conductor;
a signal cable electrically connected to the second mounting terminal; and
solder that electrically connects the third mounting terminal and the signal cable, wherein
the third mounting terminal includes a terminal-front-end portion, and the terminal-front-end portion is located at a position apart from a connection surface between the second mounting terminal and the signal cable,
the signal cable includes: a conductor, a coated portion, and a cable boundary portion located at a boundary between the conductor and the coated portion,
the cable boundary portion is located outside the second end face,
the solder coats the third mounting terminal and the conductor so as to form a curved surface that extends from the terminal-front-end portion to the cable boundary portion, and
the connector, the signal cable, and the solder are positioned within a region surrounded by an external outline of the solid-state image sensing device as seen in the direction from the solid-state image sensing device to the second end face.

2. The imaging module according to claim 1, wherein a shape of the connector is a rectangular parallelepiped having at least the first end face, the second end face, and the side face.

3. The imaging module according to claim 1, wherein the connector comprises: a first side face and a second side face which are orthogonal to the first end face, and a groove provided between the first side face and the second side face,
the second mounting terminal is provided in the groove, and
the signal cable is located in the groove and is electrically connected to the second mounting terminal.

4. The imaging module according to claim 3, wherein the second side face is orthogonal to the first end face and the first side face,
a first virtual extension surface of the first side face and a second virtual extension surface of the second side face intersect with each other at an intersection point,
the groove is a region surrounded by walls connected to the first side face and the second side face, the first virtual extension surface, and the second virtual extension surface, and
the second mounting terminal is electrically connected to the signal cable inside the groove.

5. The imaging module according to claim 4, further comprising:
a plurality of grooves, each of which is provided at a corner region of the connector; and
a plurality of second mounting terminals, each of which is provided so as to correspond to one groove, wherein
each second mounting terminal is provided inside one groove, and
the plurality of the second mounting terminals are located at positions at which the second mounting terminals face each other.

6. The imaging module according to claim 1, wherein the first mounting terminal constitutes part of the implanted conductor.

7. The imaging module according to claim 1, wherein the implanted conductor extends from the first end face to the second end face and is implanted in the inside of the main body.

8. The imaging module according to claim 1, wherein the implanted conductor comprises:
an internal conductor that extends in a direction from the first end face to the second end face in the inside of the main body; and
a connection conductor that connects the internal conductor and the second mounting terminal in the inside of the main body.

9. The imaging module according to claim 1, further comprising:
a fourth mounting terminal provided on the second end face; and
an electronic component provided on the fourth mounting terminal and connected thereto.

10. An imaging module comprising:
a solid-state image sensing device comprising an imaging-device terminal;
a connector having a first end face, a second end face located opposite to the first end face, and a side face orthogonal to the first end face, the connector comprising: a main body serving as an insulating member, an implanted conductor that is implanted in an inside of the main body, a first mounting terminal that is electrically connected to the imaging-device terminal and the implanted conductor and is provided on the first end face, an internal conductor that is connected to the first mounting terminal, extends in a direction from the first end face toward the second end so as to reach an inner end located inside the main body, and constitutes part of the implanted conductor, a connection conductor that is connected to the internal conductor and extends from the inner end toward an outside of the main body, a second mounting terminal that is connected to the connection conductor, is provided on the side face, and constitutes part of the implanted conductor, and a third mounting terminal that is connected to the second mounting terminal, is provided on the second end face, and constitutes part of the implanted conductor; and
a signal cable electrically connected to the second mounting terminal.

11. The imaging module according to claim 10, wherein the implanted conductor is an integrally molded member formed in the connector, and
in a cross-sectional view, the implanted conductor is surrounded by:
a first surface of the first mounting terminal;
a first contact surface that is continuously connected to the first surface of the first mounting terminal and is located between the internal conductor and the insulating member;
a second contact surface that is continuously connected to the first contact surface and is located between the connection conductor and the insulating member;
a second surface of the second mounting terminal which is continuously connected to the second contact surface;
a third contact surface that is located between the second mounting terminal and the insulating member;
a third surface of the third mounting terminal which is continuously connected to the second surface; and
a fourth contact surface that is located between the third mounting terminal and the insulating member.

* * * * *